(12) United States Patent
Kimura et al.

(10) Patent No.: US 10,809,530 B2
(45) Date of Patent: Oct. 20, 2020

(54) INFORMATION PROCESSING APPARATUS AND INFORMATION PROCESSING METHOD

(71) Applicant: SONY CORPORATION, Tokyo (JP)

(72) Inventors: Jun Kimura, Kanagawa (JP); Tsubasa Tsukahara, Tokyo (JP); Ryo Fukazawa, Kanagawa (JP); Tomohisa Tanaka, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/781,912

(22) PCT Filed: Dec. 6, 2016

(86) PCT No.: PCT/JP2016/086130
§ 371 (c)(1),
(2) Date: Jun. 6, 2018

(87) PCT Pub. No.: WO2017/115618
PCT Pub. Date: Jul. 6, 2017

(65) Prior Publication Data
US 2018/0356636 A1 Dec. 13, 2018

(30) Foreign Application Priority Data

Dec. 28, 2015 (JP) ................................ 2015-257065

(51) Int. Cl.
*G02B 27/01* (2006.01)
*G06F 3/01* (2006.01)
*G06K 9/00* (2006.01)

(52) U.S. Cl.
CPC ....... *G02B 27/0172* (2013.01); *G02B 27/017* (2013.01); *G02B 27/0176* (2013.01);
(Continued)

(58) Field of Classification Search
CPC .............. G02B 27/0172; G02B 27/017; G02B 27/0176; G02B 27/0179; G02B 2027/014;
(Continued)

(56) References Cited

U.S. PATENT DOCUMENTS

| 2008/0062297 A1 | 3/2008 | Sako et al. |
| 2014/0098126 A1* | 4/2014 | Fein ........................ G06T 11/00 345/633 |

(Continued)

FOREIGN PATENT DOCUMENTS

| CN | 101141567 A | 3/2008 |
| CN | 101414251 A | 4/2009 |

(Continued)

OTHER PUBLICATIONS

International Search Report and Written Opinion of PCT Application No. PCT/JP2016/086130, dated Feb. 22, 2017, 09 pages of ISRWO.

(Continued)

*Primary Examiner* — Peter D McLoone
(74) *Attorney, Agent, or Firm* — Chip Law Group

(57) ABSTRACT

An information processing apparatus including circuitry that acquires information associated with a user situation, determines a display mode based on the information associated with the user situation, and enables an operation unit to receive a user input based on a target displaying in the determined display mode.

7 Claims, 26 Drawing Sheets

(52) U.S. Cl.
CPC .......... *G02B 27/0179* (2013.01); *G06F 3/011* (2013.01); *G06F 3/012* (2013.01); *G06F 3/013* (2013.01); *G06K 9/00778* (2013.01); *G02B 2027/014* (2013.01); *G02B 2027/0178* (2013.01); *G02B 2027/0183* (2013.01); *G02B 2027/0187* (2013.01)

(58) Field of Classification Search
CPC .... G02B 2027/0178; G02B 2027/0183; G02B 2027/187; G06F 3/011; G06F 3/012; G06F 3/013; G06K 9/00778
See application file for complete search history.

(56) References Cited

U.S. PATENT DOCUMENTS

2015/0277699 A1* 10/2015 Algreatly ............ G06F 3/04815
715/850
2016/0239081 A1 8/2016 Imoto et al.

FOREIGN PATENT DOCUMENTS

| CN | 105765513 A | 7/2016 |
|----|-------------|--------|
| EP | 1898634 A2 | 3/2008 |
| EP | 2048875 A2 | 4/2009 |
| EP | 3065040 A1 | 9/2016 |
| JP | 2008-067218 A | 3/2008 |
| WO | 2015/064165 A1 | 5/2015 |

OTHER PUBLICATIONS

Office Action for EP Patent Application No. 16816755.9, dated Apr. 17, 2019, 04 pages of Office Action.

Office Action for JP Patent Application No. 2015-257065, dated Mar. 3, 2020, 05 pages of Office Action and 06 pages of English Translation.

Office Action for CN Patent Application No. 201680075071.5, dated Apr. 29, 2020, 7 pages of Office Action and 9 pages of English Translation.

* cited by examiner

[Fig. 1]
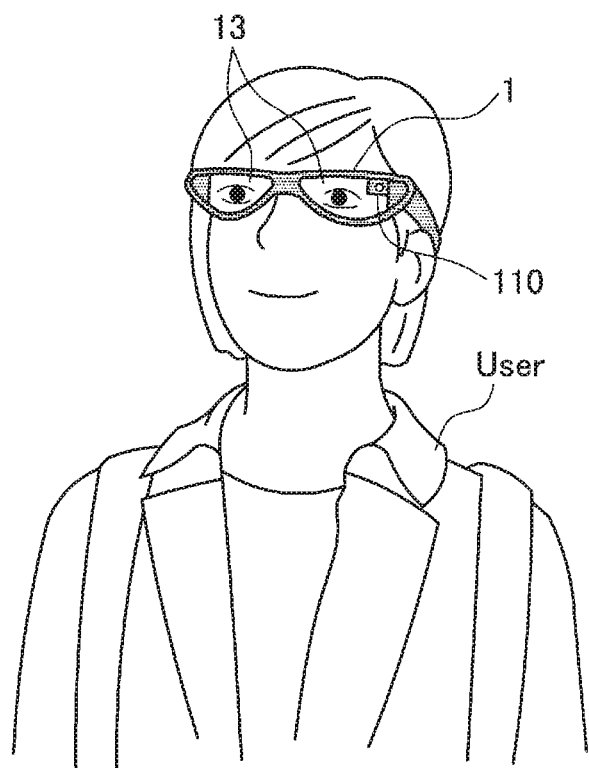

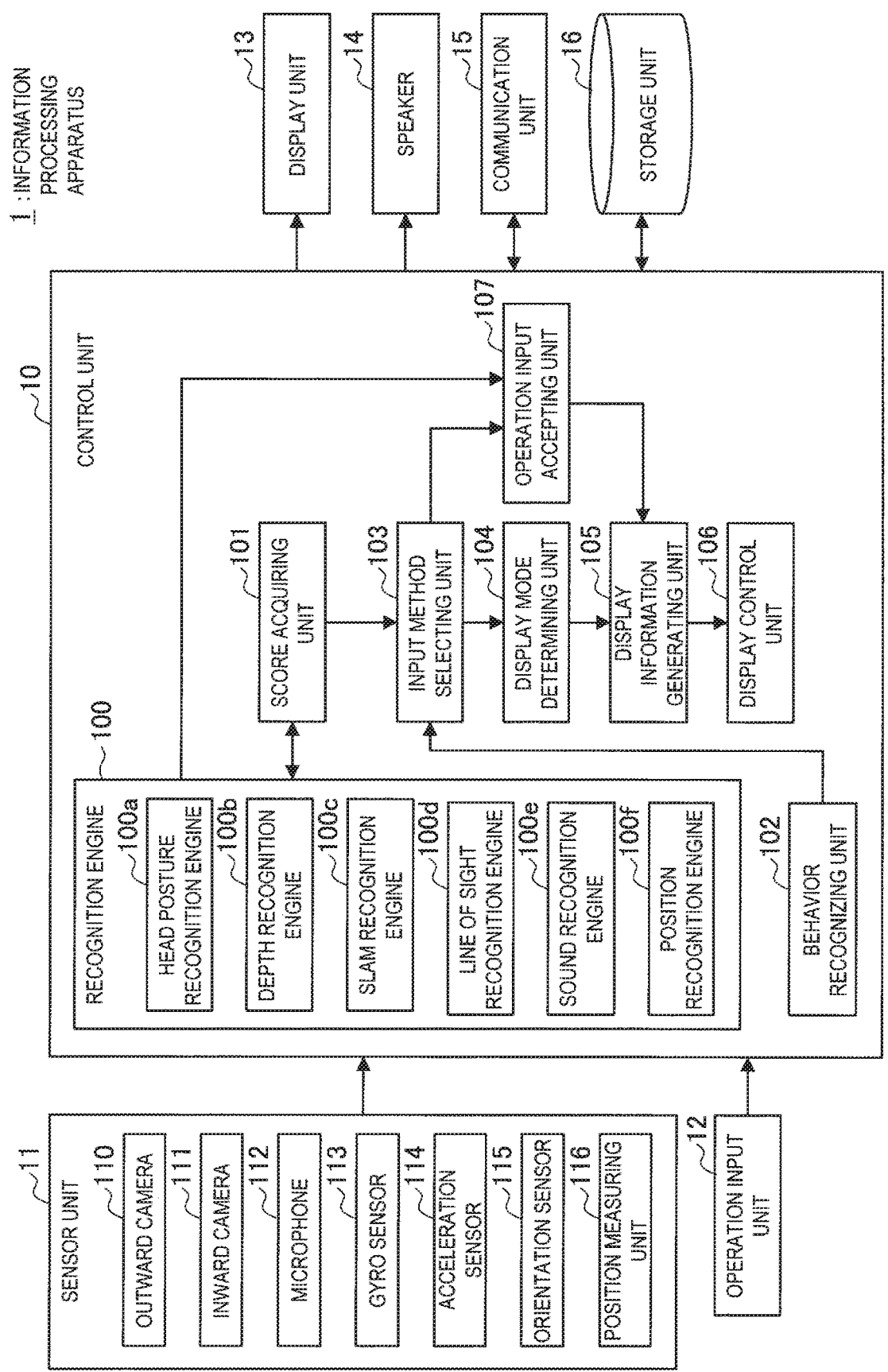
[Fig. 2]

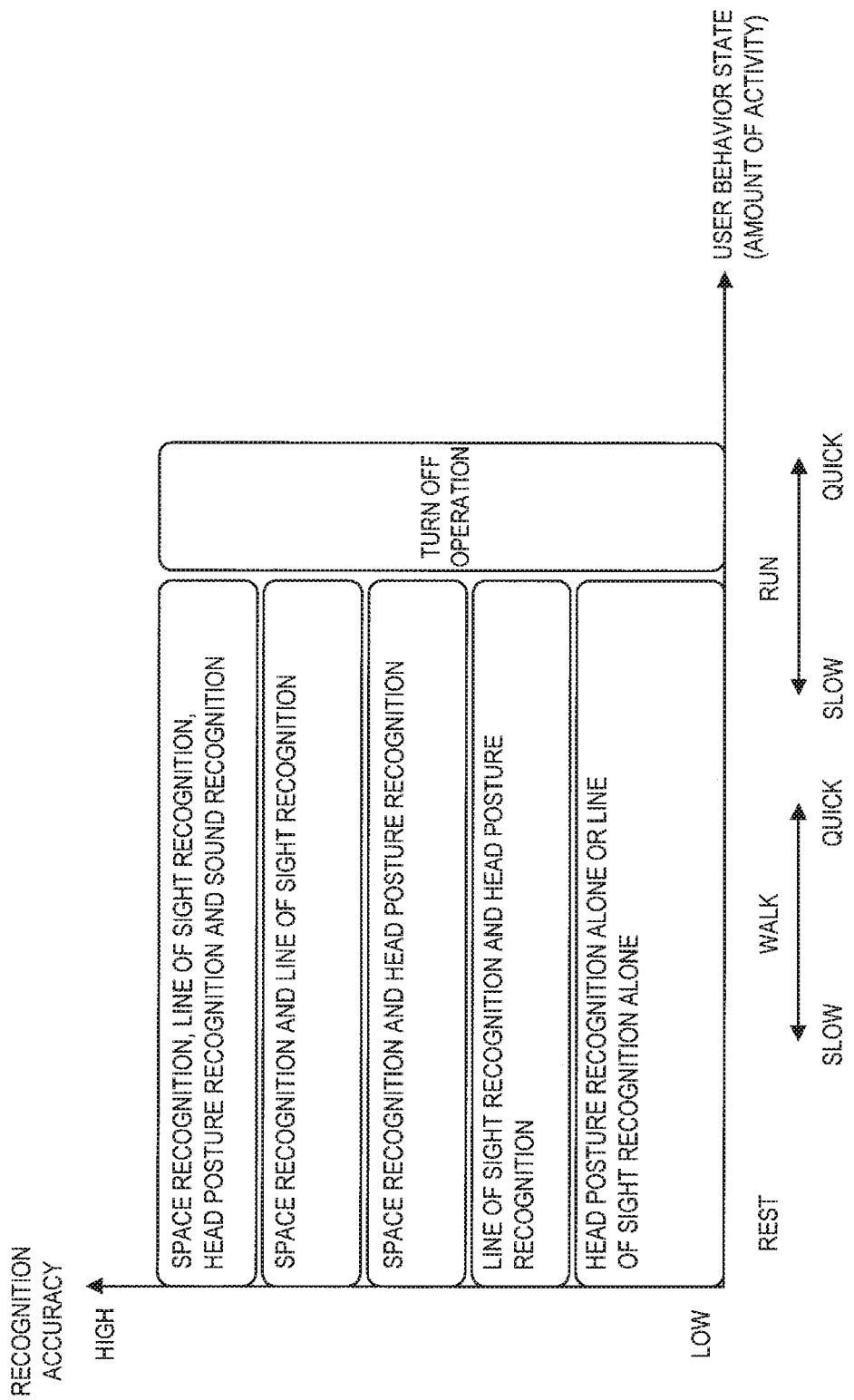
[Fig. 3]

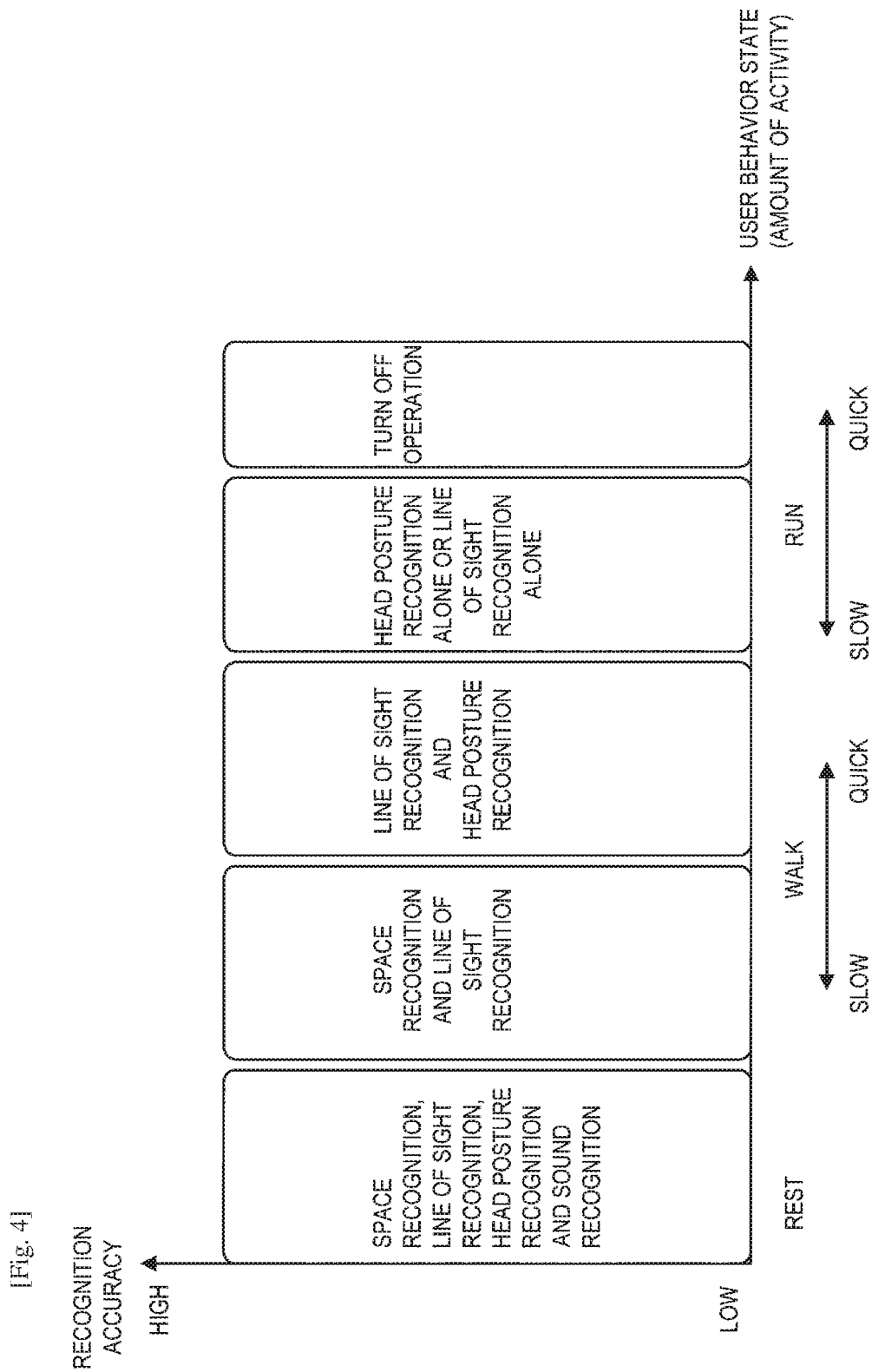
[Fig. 4]

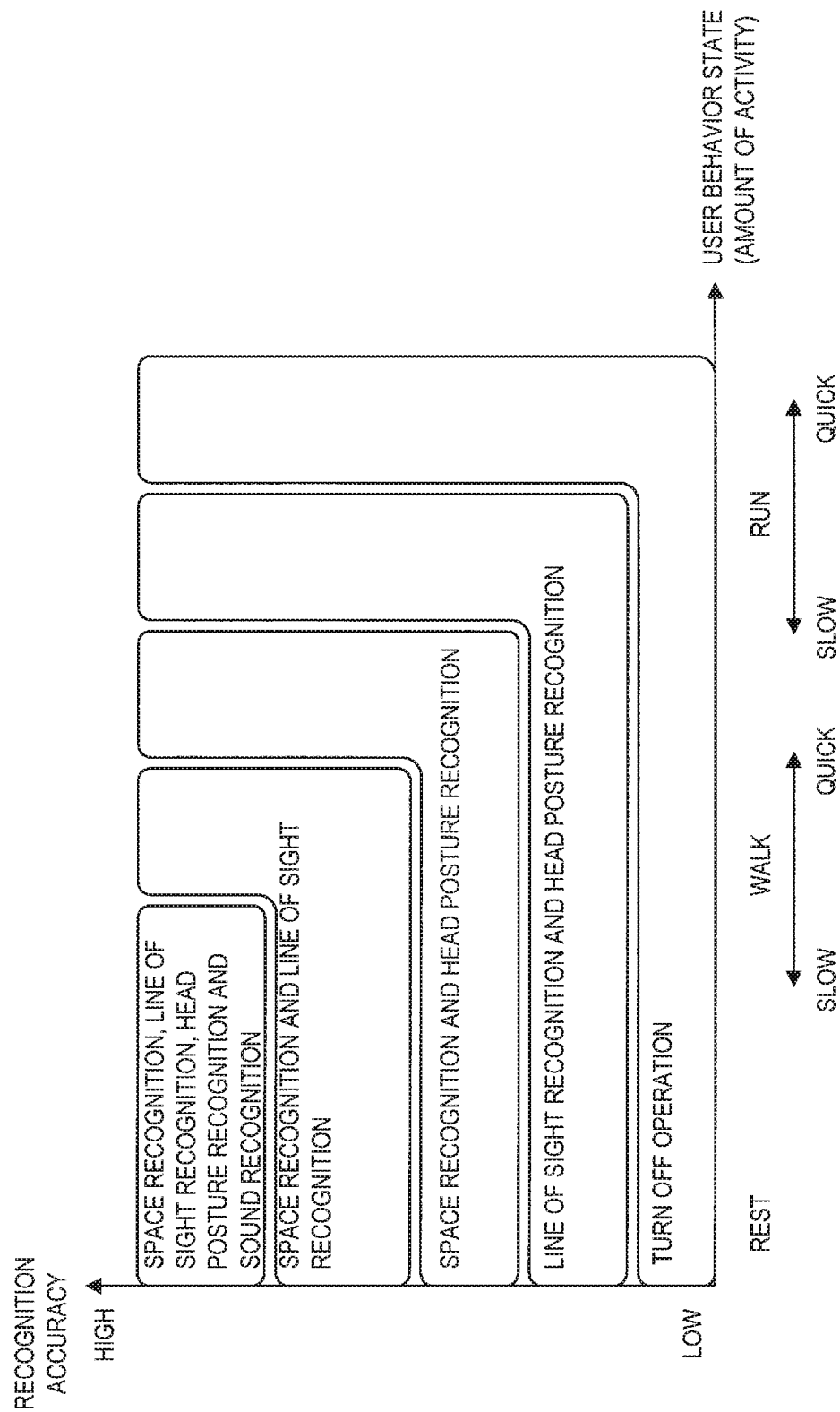

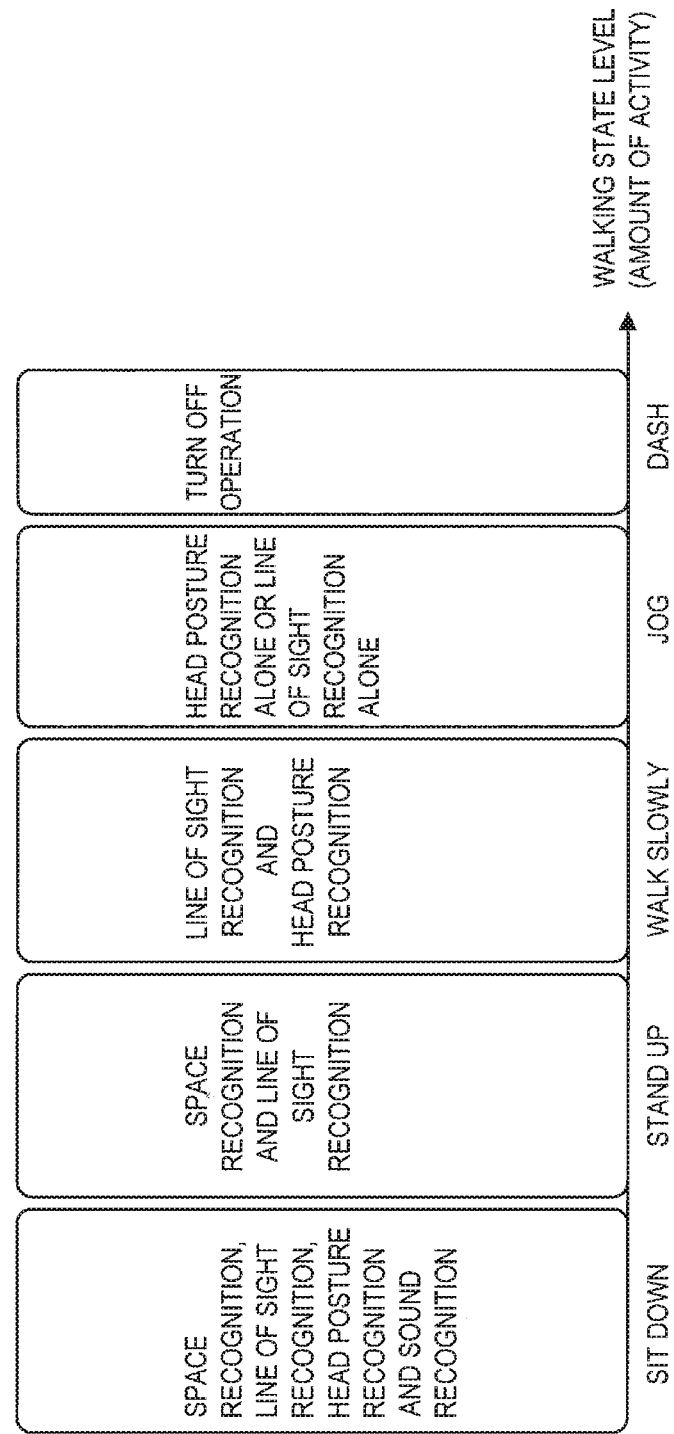
[Fig. 6]

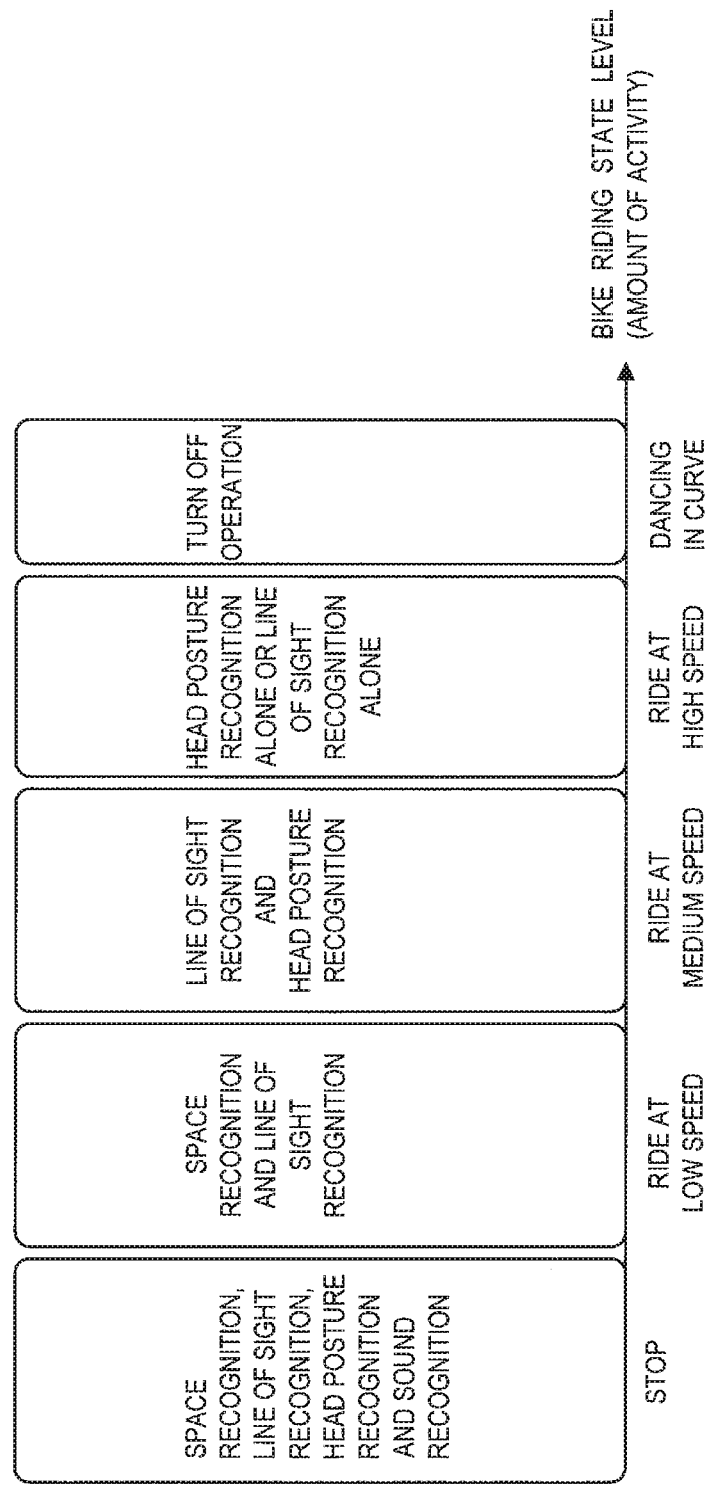

[Fig. 8]
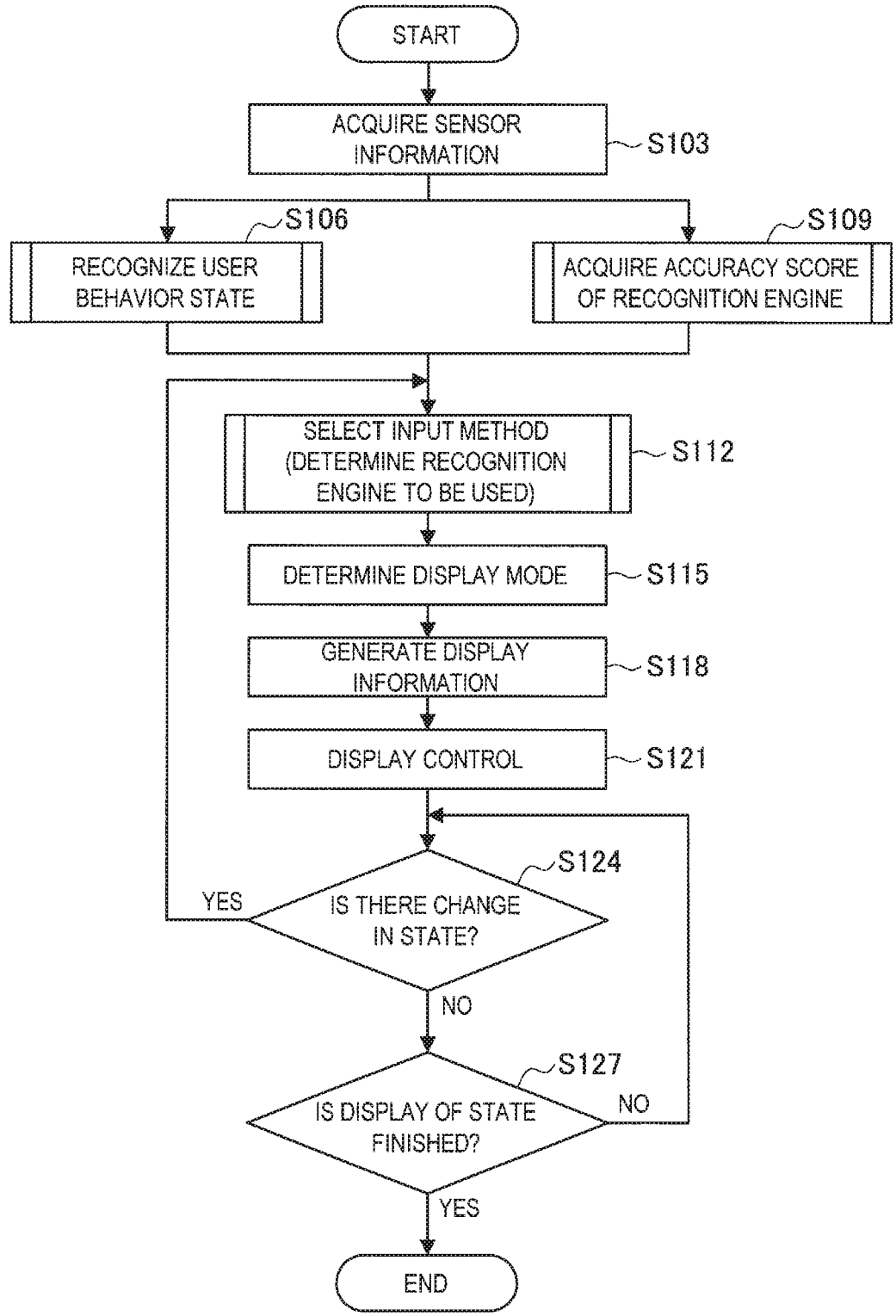

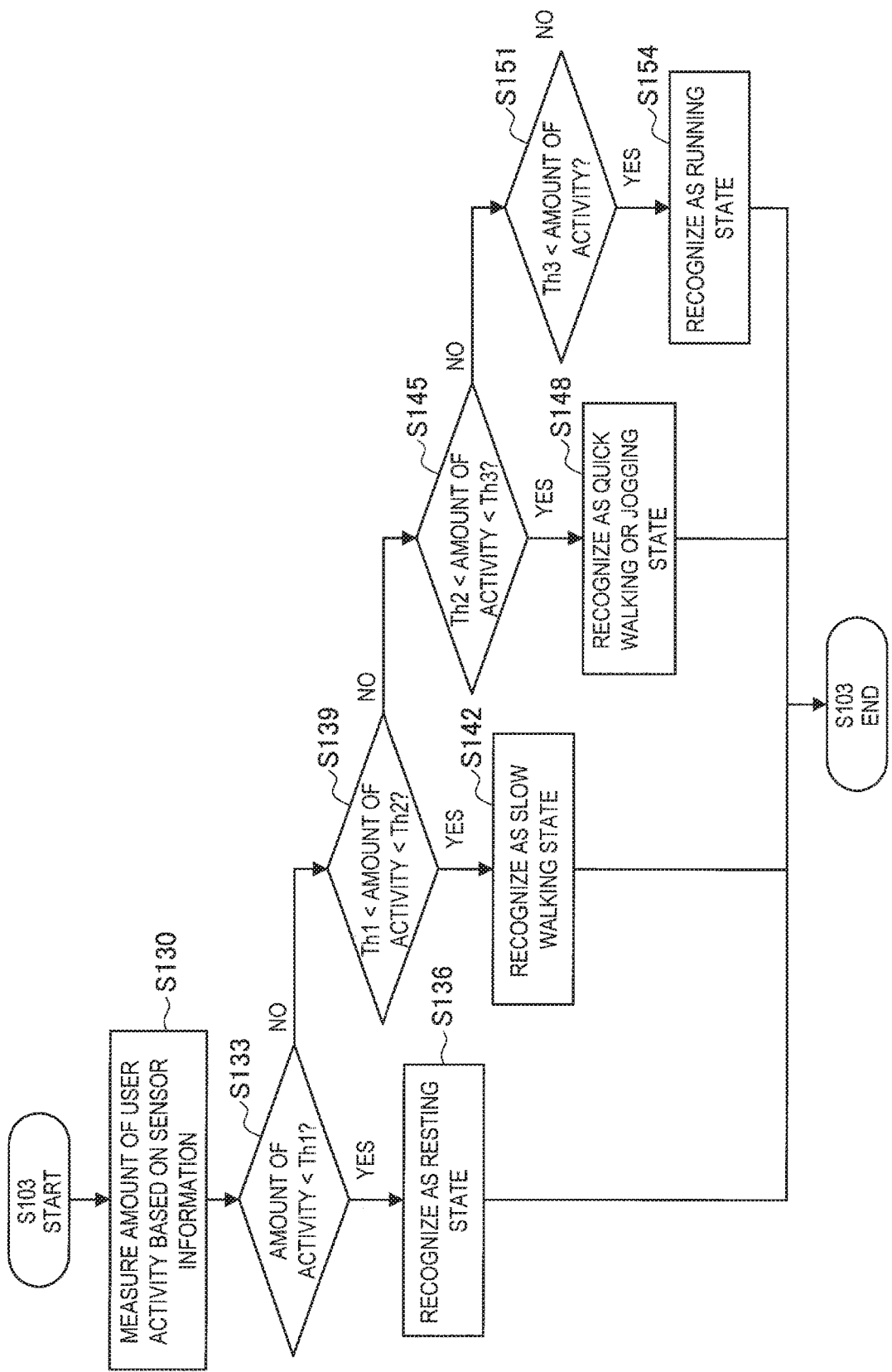
[Fig. 9]

[Fig. 10]
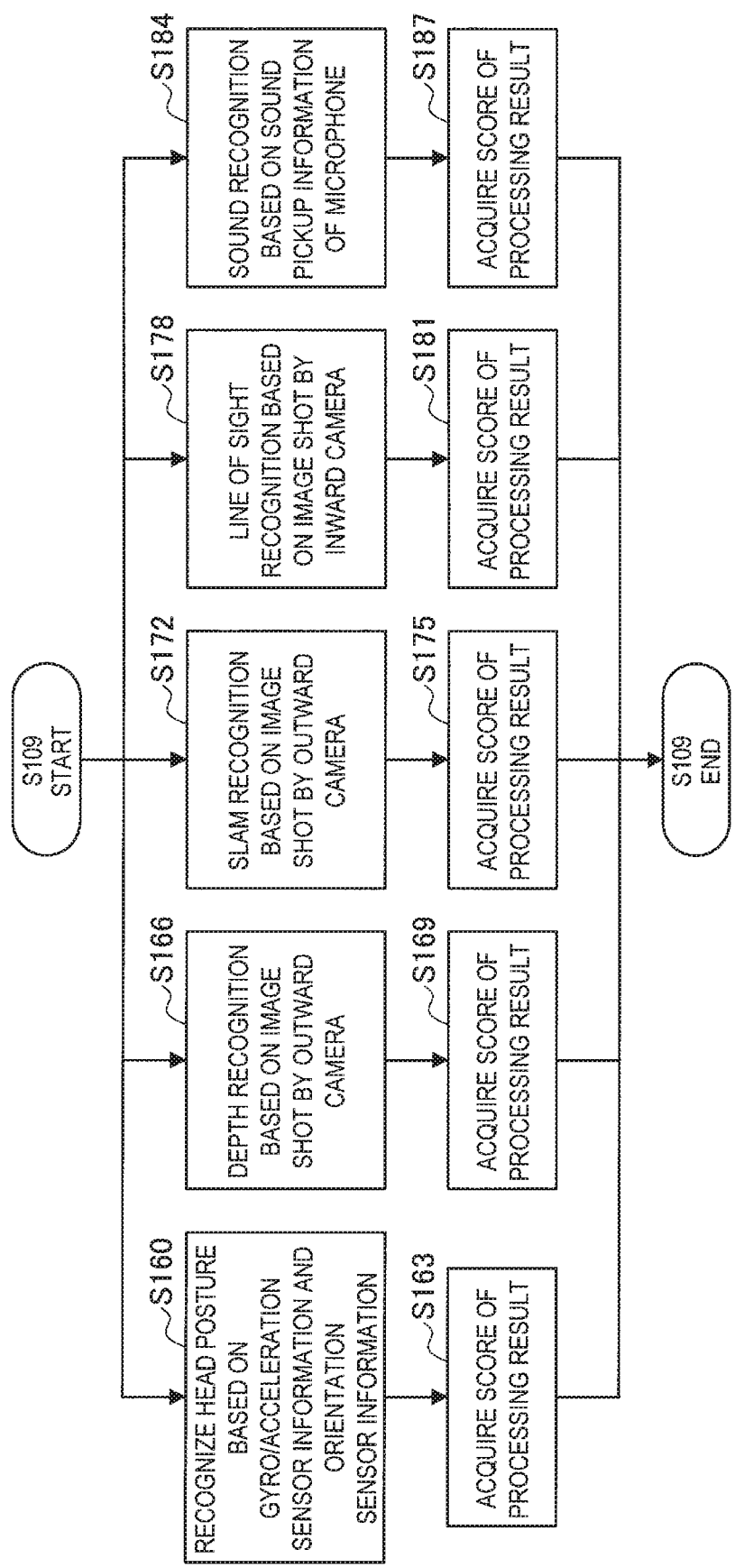

[Fig. 11]
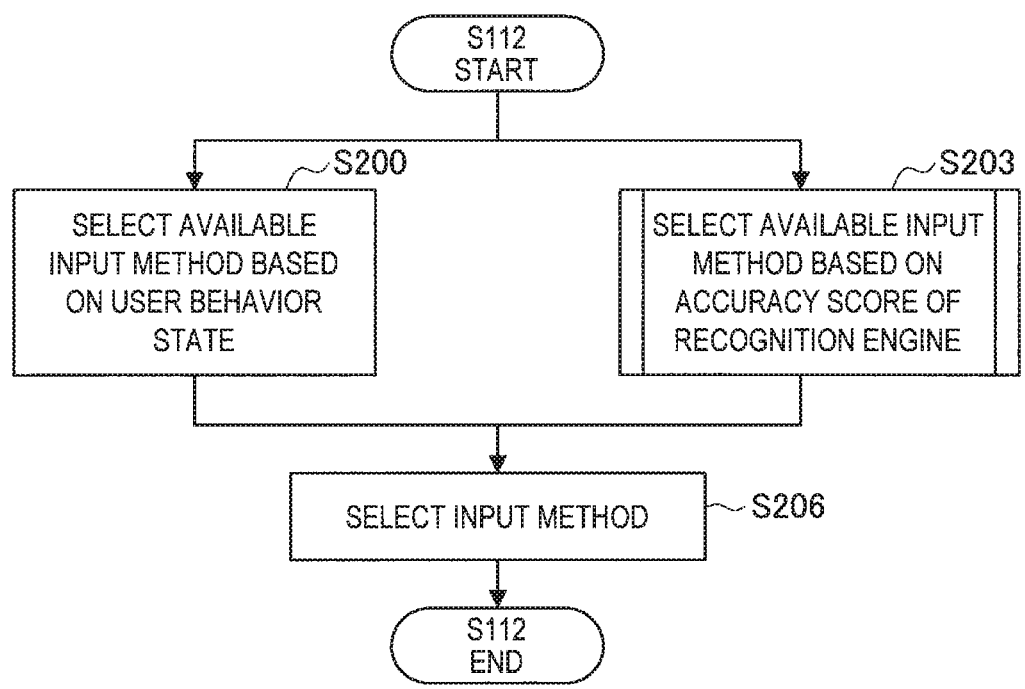

[Fig. 12]
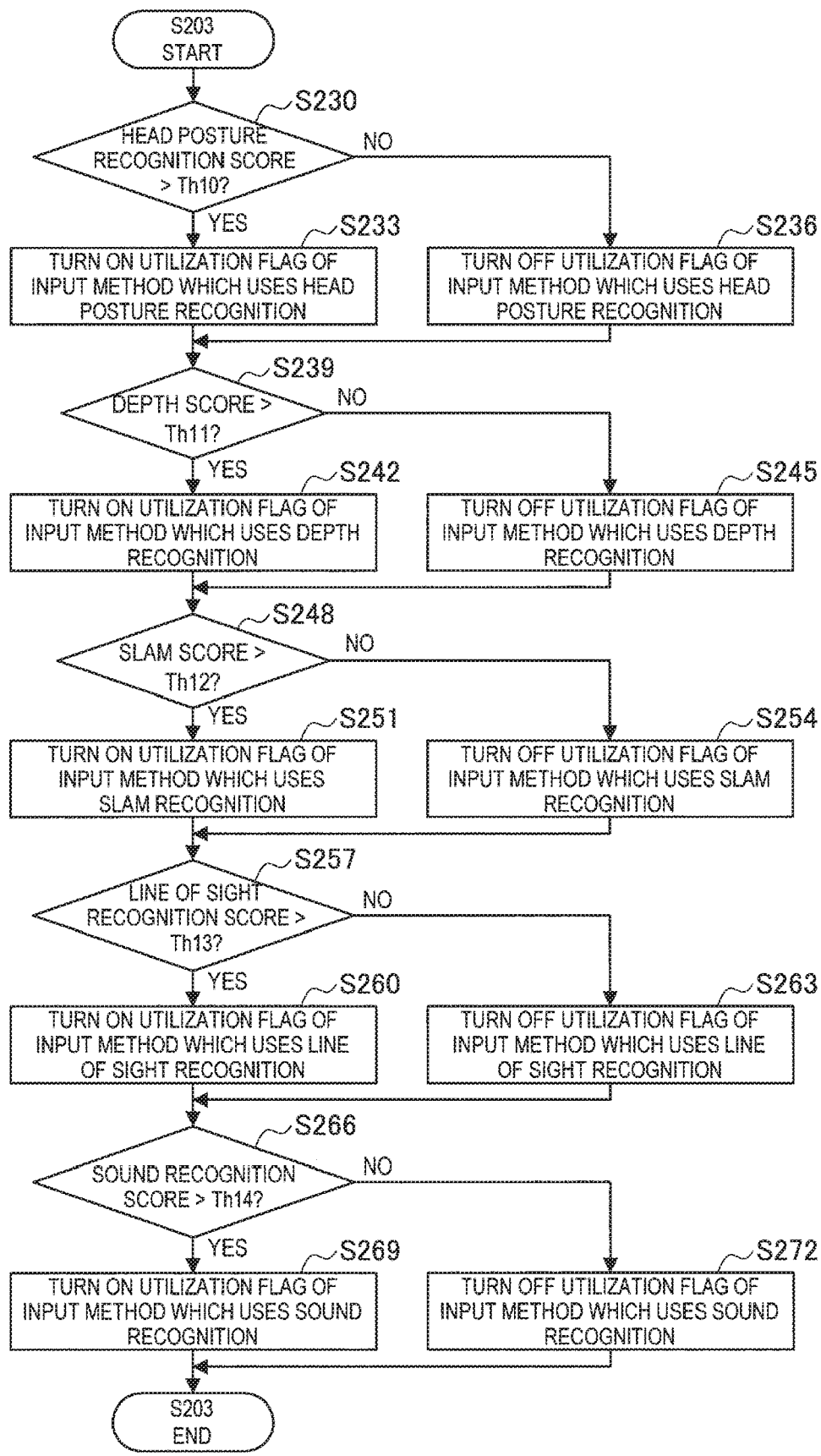

[Fig. 13]
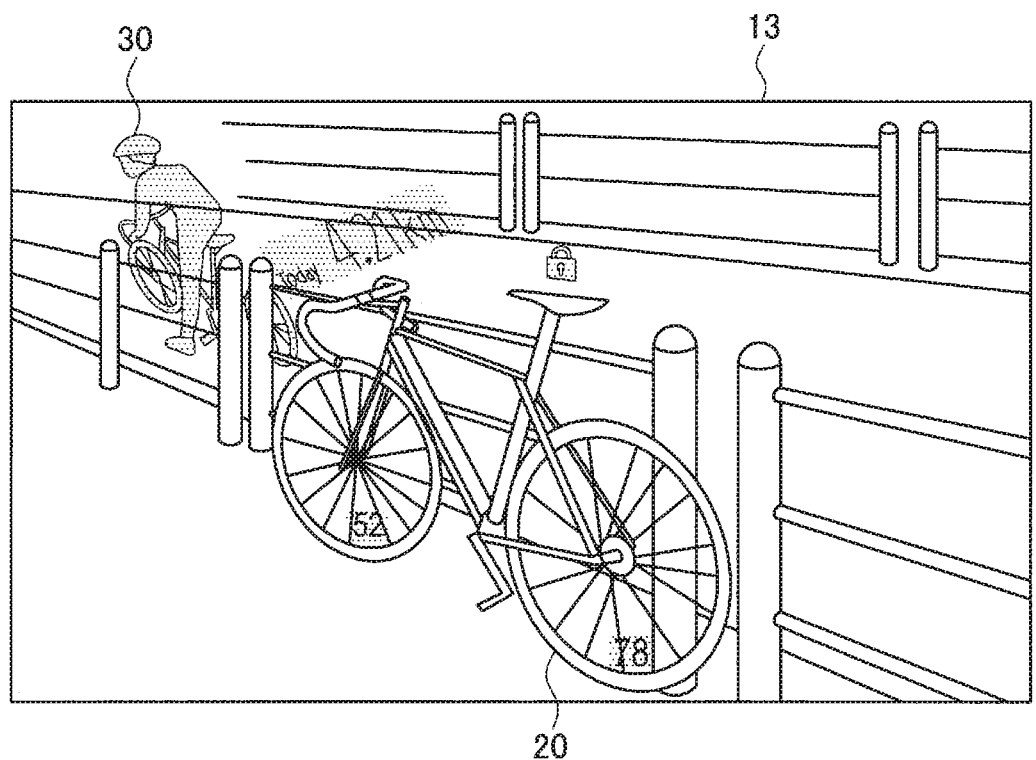
[Fig. 14]
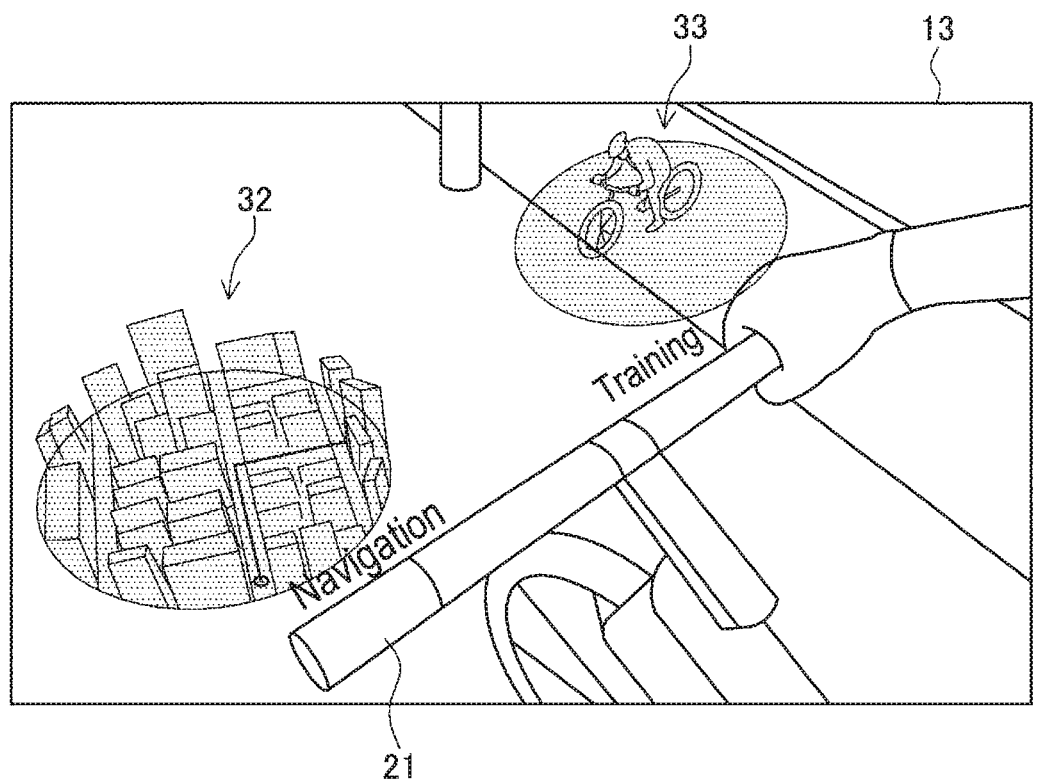

[Fig. 15]
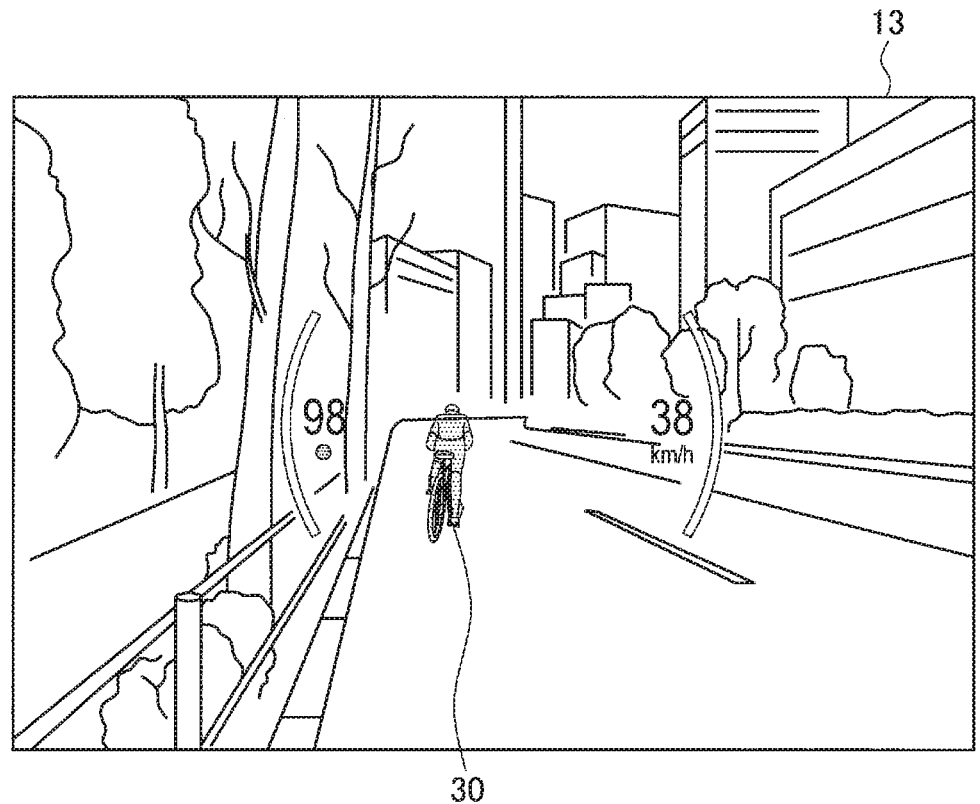
[Fig. 16]
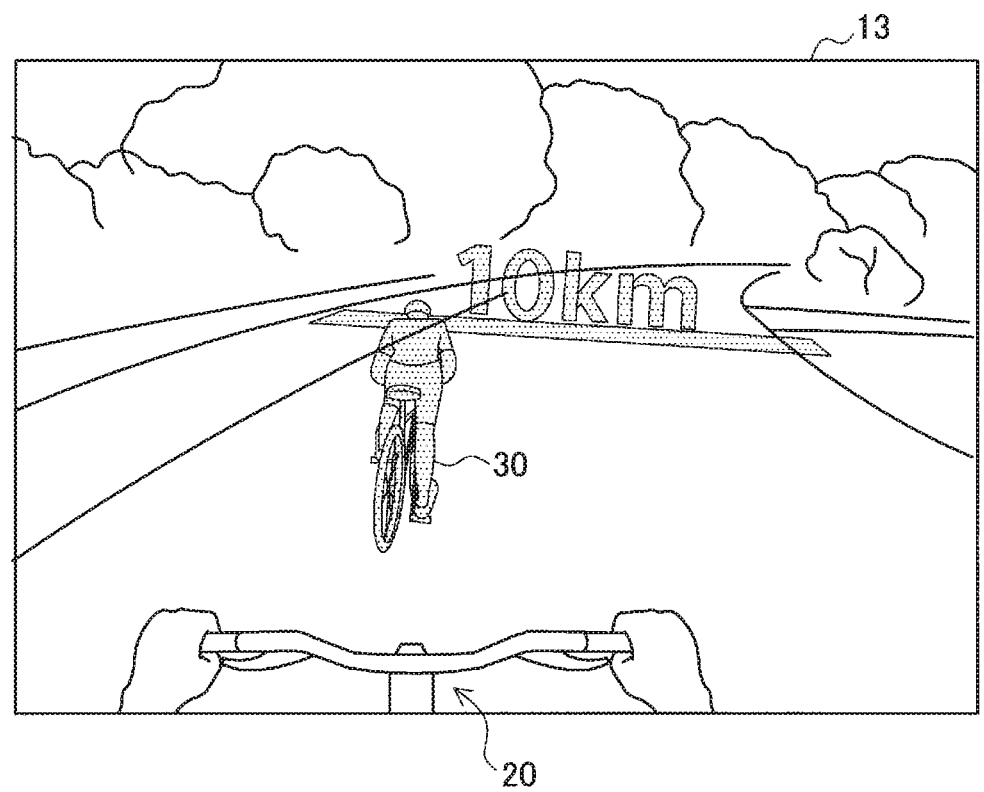

[Fig. 17]
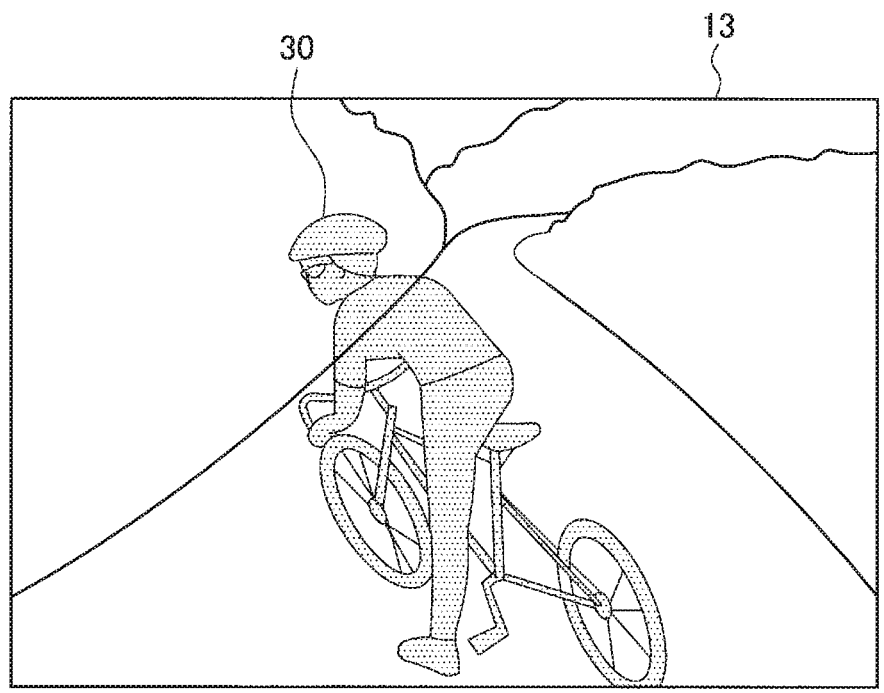

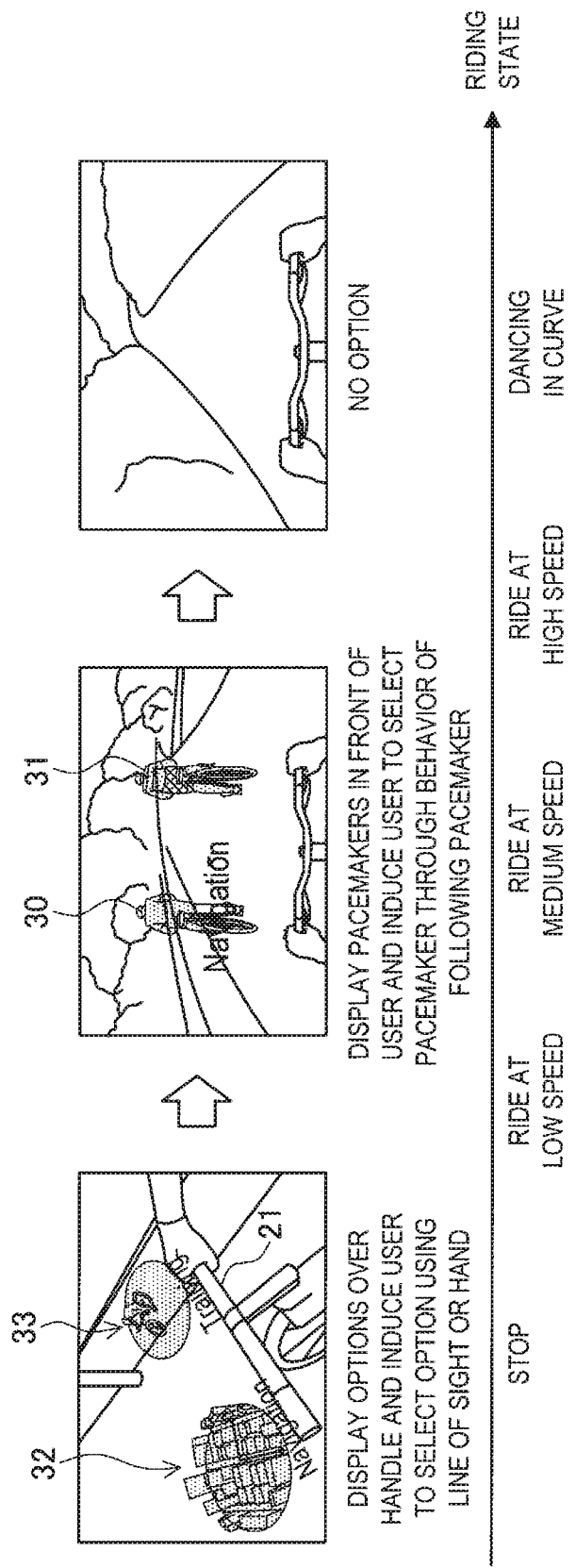

[Fig. 19]
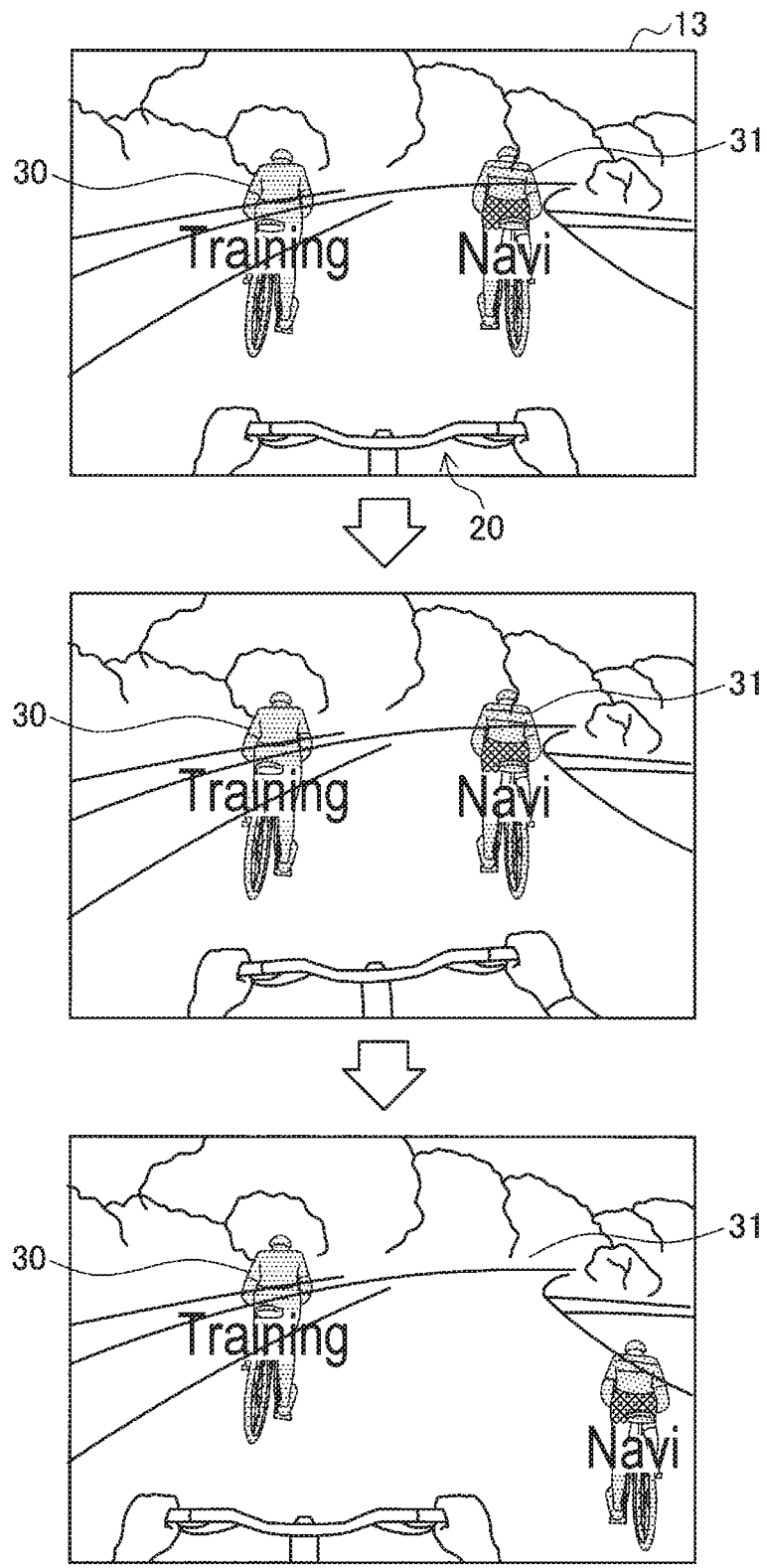

[Fig. 20]
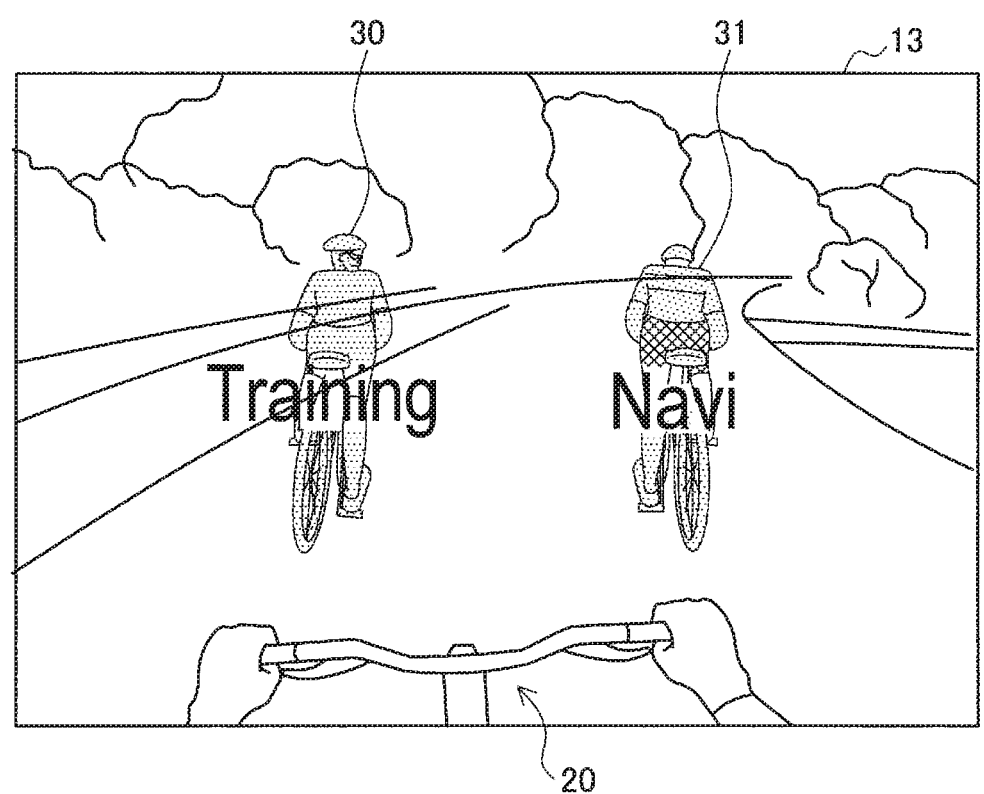

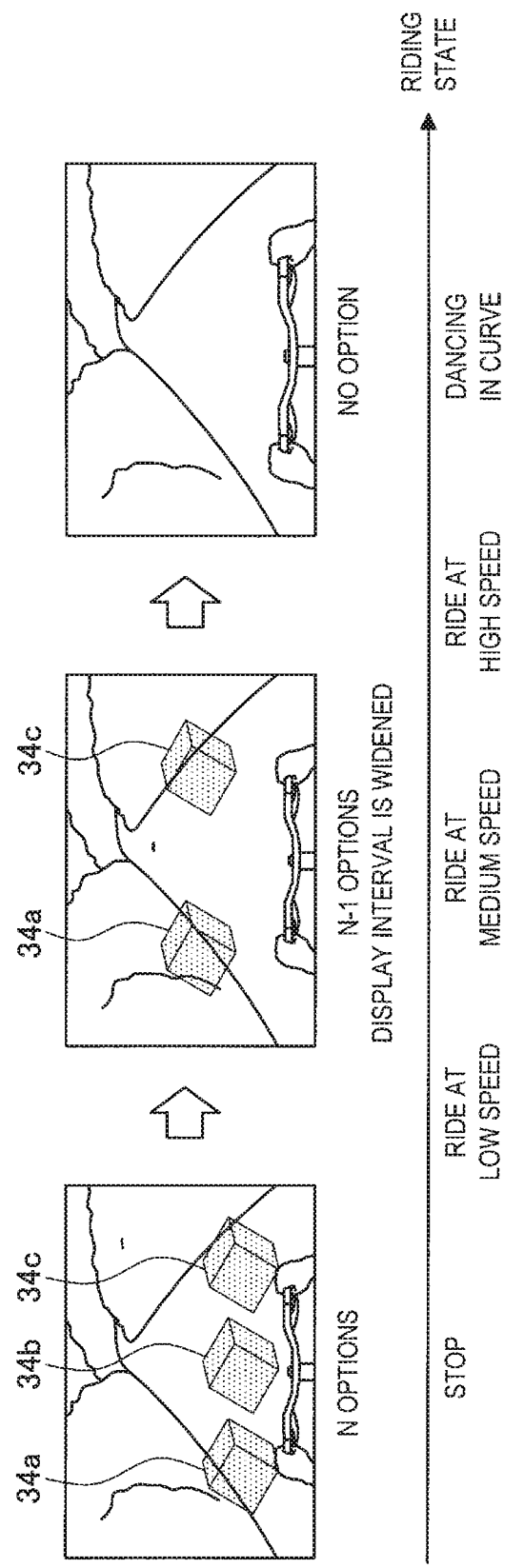
[Fig. 21]

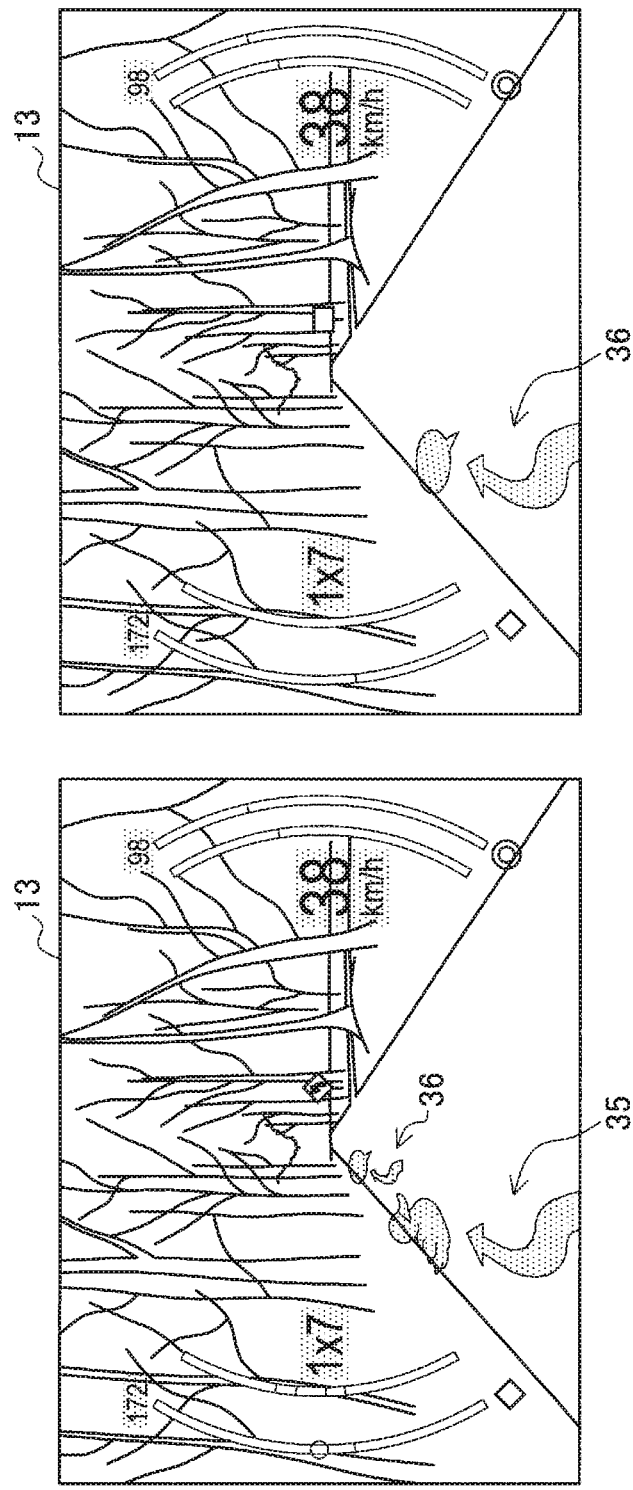
[Fig. 22]

[Fig. 23]
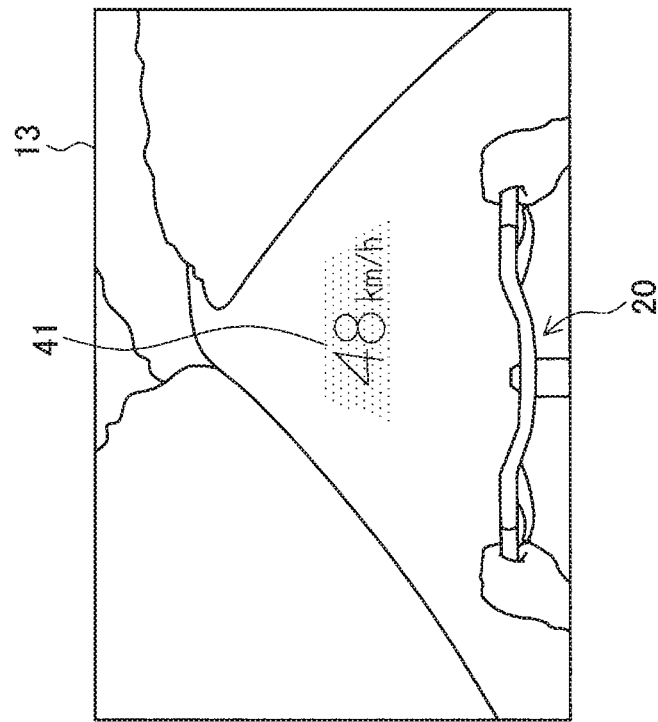
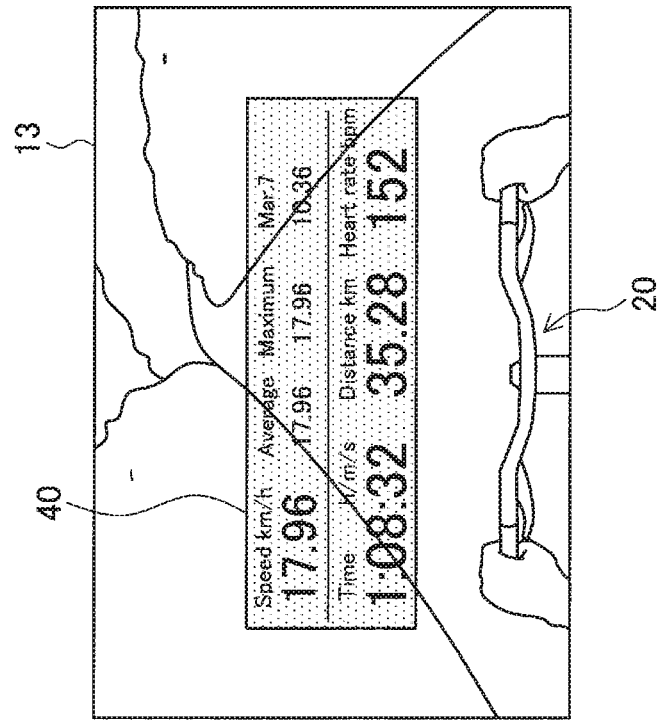

[Fig. 24]
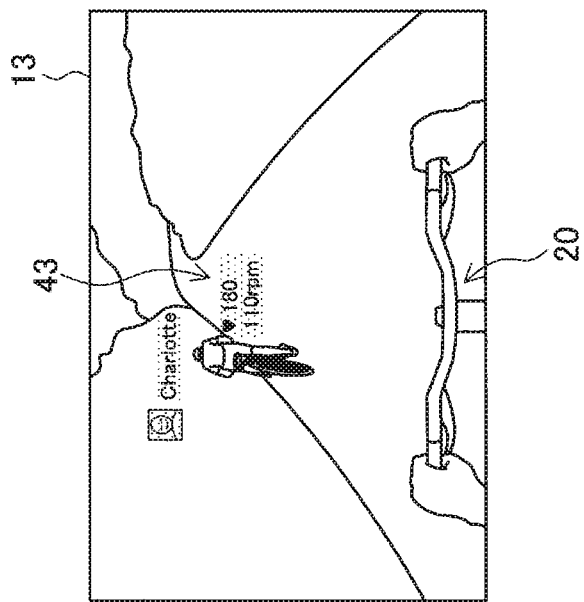
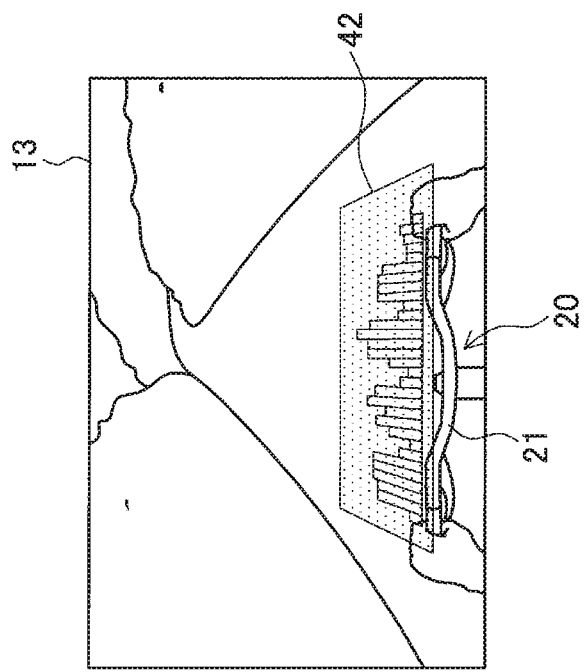

[Fig. 25]
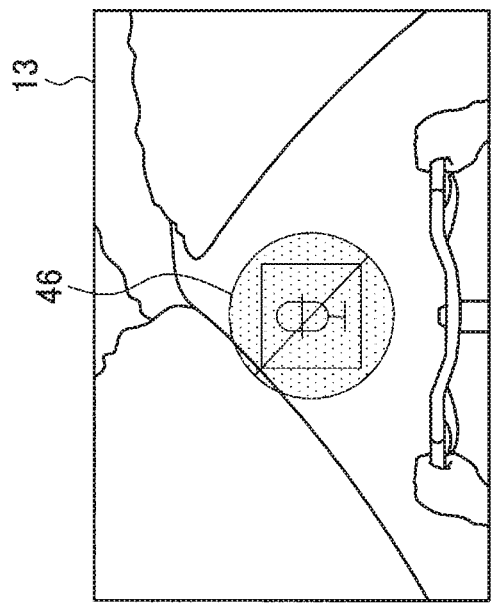
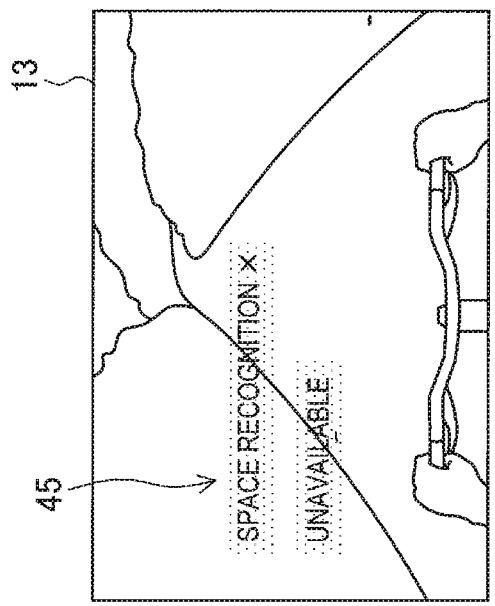
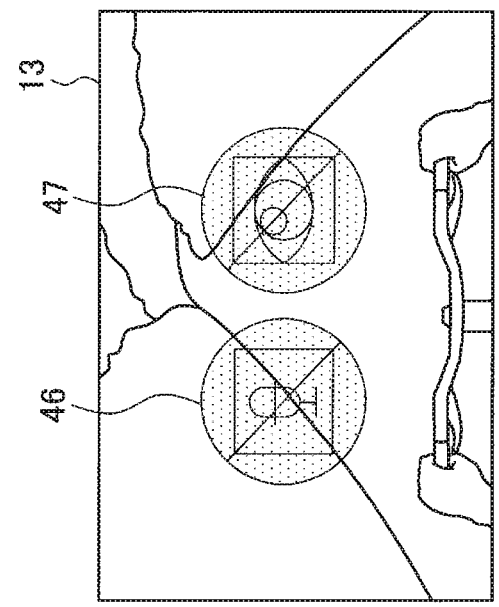

[Fig. 26]
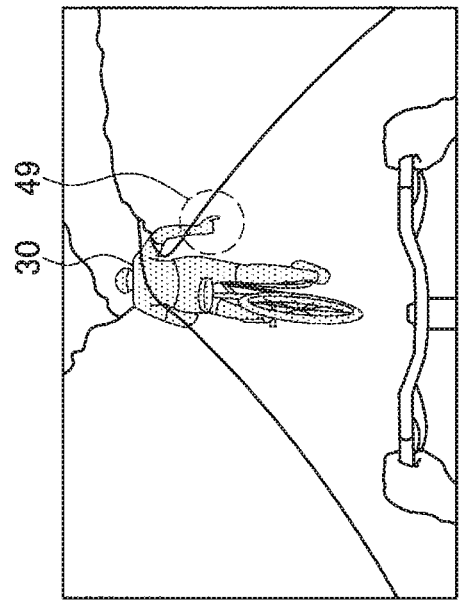
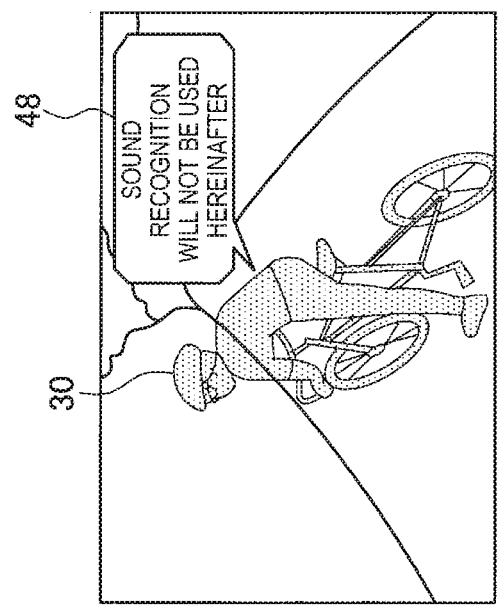

[Fig. 27]
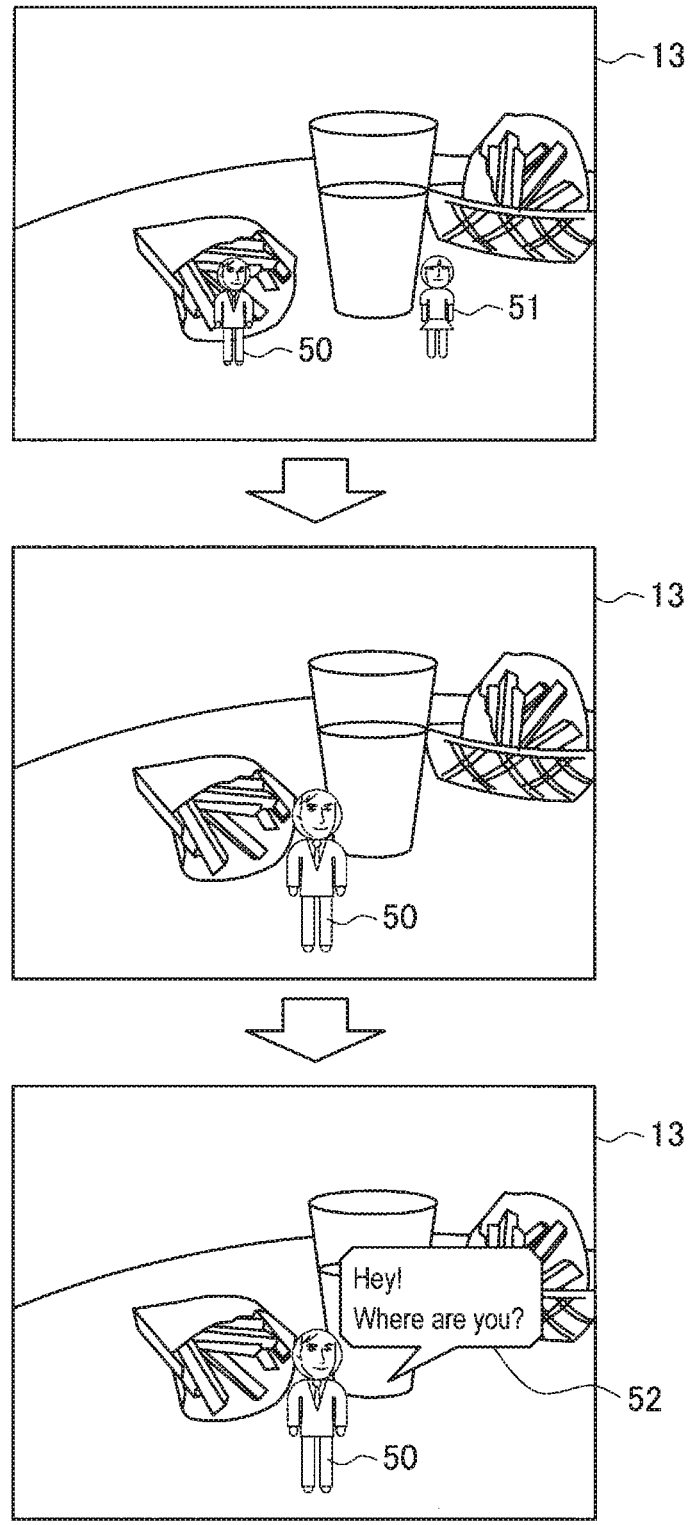

[Fig. 28]
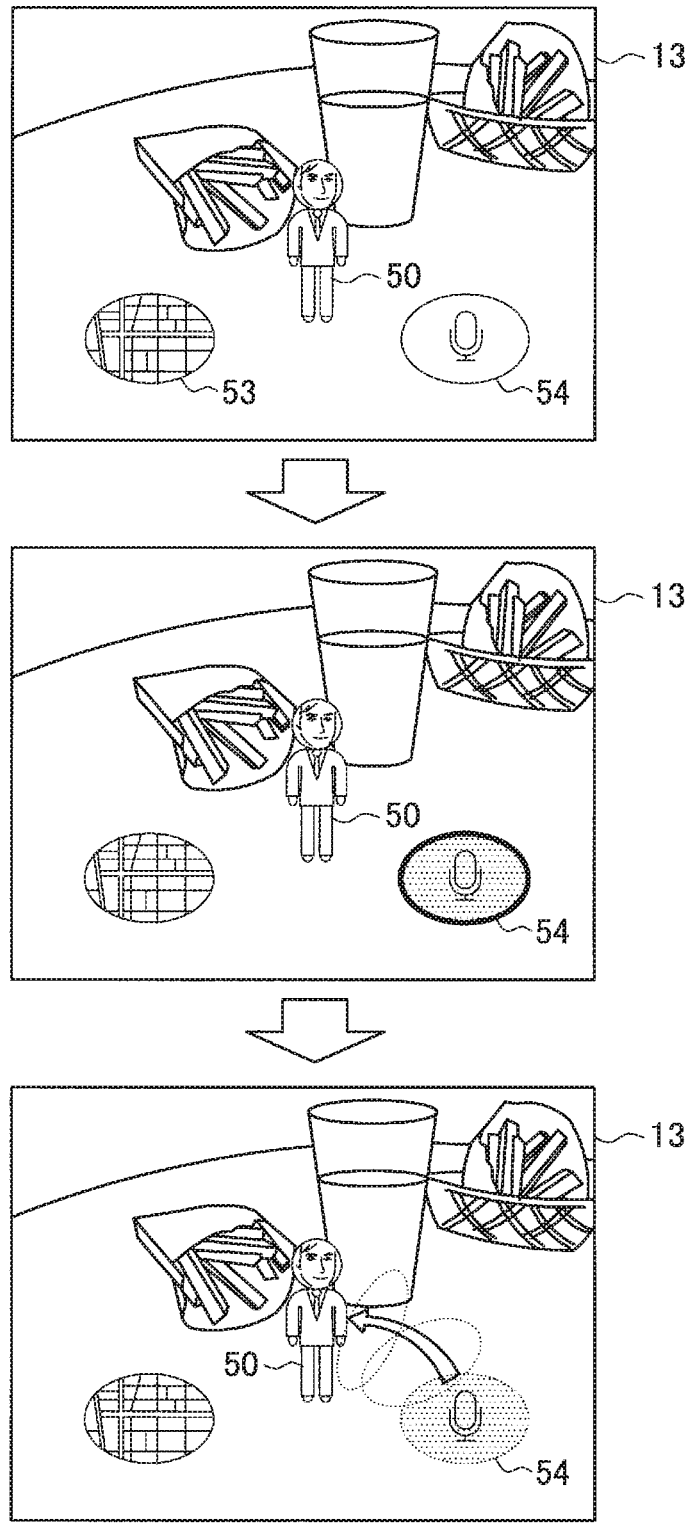

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2016/086130 filed on Dec. 6, 2016, which claims the priority benefit of Japanese Priority Patent Application No. JP 2015-257065 filed in the Japan Patent Office on Dec. 28, 2015. Each of the above-referenced applications is hereby incorporated herein by reference in its entirety.

TECHNICAL FIELD

The present disclosure relates to an information processing apparatus, an information processing method, and a program.

BACKGROUND ART

In recent years, a head mounted display (hereinafter, also referred to as an "HMD") provided with an operation device has been developed. The HMD which has a display located in front of eyes of a user when the HMD is worn on the head of the user, displays a display object in front of the user. Such an HMD includes a non-transmissive display or a transmissive display.

In the case of a transmissive display, the above-described display object is displayed while the display object is superimposed on real space which can be viewed through the display. For example, with the HMD of the following PTL 1, a display object which moves in parallel to a display surface is displayed in front of the user, while a cursor for selecting the display object moves on a display axis according to user operation detected by the operation device.

CITATION LIST

Patent Literature

[PTL 1]
JP 2014-164449A

SUMMARY

Technical Problem

With the above-described PTL 1, user operation is improved by performing display control so that a display axis has a vertical component according to user operation. However, it is difficult to input operation with the same accuracy depending on a state of user behavior, for example, when the user stops or while the user moves, and operability degrades.

Therefore, the present disclosure proposes an information processing apparatus, an information processing method and a program which can further improve operability by dynamically switching an input method according to a state of user activity.

Solution to Problem

According to an embodiment of the present disclosure, there is provided an information processing apparatus including circuitry configured to acquire information associated with a user situation, determine a display mode based on the information associated with the user situation, and allow an operation unit to receive a user input based on a target displaying in the determined display mode.

According to an embodiment of the present disclosure, there is provided an information processing method including acquiring information associated with a user situation; determining a display mode based on the information associated with the user situation, and allowing an operation unit to receive a user input based on a target displaying in the determined display mode.

According to an embodiment of the present disclosure, there is provided a non-transitory computer-readable storage medium having embodied thereon a program, which when executed by a computer causes the computer to execute a method, the method including acquiring information associated with a user situation; determining a display mode based on the information associated with the user situation, and allowing an operation unit to receive a user input based on a target displaying in the determined display mode.

Advantageous Effects of Invention

As described above, according to an embodiment of the present disclosure, it is possible to further improve operability by dynamically switching an operation input mode according to a state of user activity.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 1 is a diagram explaining outline of an information processing apparatus according to an embodiment.

FIG. 2 is a block diagram illustrating an example of a configuration of the information processing apparatus according to an embodiment.

FIG. 3 is a diagram explaining a case where an operation input mode is switched according to recognition accuracy according to an embodiment.

FIG. 4 is a diagram explaining a case where the operation input mode is switched according to a state of user behavior according to an embodiment.

FIG. 5 is a diagram explaining a case where the operation input mode is switched according to recognition accuracy and the state of user behavior according to an embodiment.

FIG. 6 is a diagram explaining a case where the operation input mode is switched according to a walking state according to an embodiment.

FIG. 7 is a diagram explaining a case where the operation input mode is switched according to a bike riding state according to an embodiment.

FIG. 8 is a flowchart illustrating display control processing according to an embodiment.

FIG. 9 is a flowchart illustrating user behavior recognition processing according to an embodiment.

FIG. 10 is a flowchart illustrating score acquisition processing according to an embodiment.

FIG. 11 is a flowchart illustrating operation input mode selection processing according to an embodiment.

FIG. 12 is a flowchart illustrating operation input mode selection processing based on a recognition accuracy score according to an embodiment.

FIG. 13 is a diagram illustrating a display example of a bike UI before a user gets on a bike according to an embodiment.

FIG. 14 is a diagram illustrating a display example of the bike UI when the user gets on the bike according to an embodiment.

FIG. 15 is a diagram illustrating a display example of the bike UI when the user rides the bike according to an embodiment.

FIG. 16 is a diagram illustrating a display example of the bike UI when the user reaches the finish line according to an embodiment.

FIG. 17 is a diagram illustrating a display example of the bike UI when a pacemaker stops according to user behavior according to an embodiment.

FIG. 18 is a diagram explaining switching of the operation input mode according to a state of user behavior in the bike UI according to an embodiment.

FIG. 19 is a diagram explaining user selection behavior in the bike UI according to an embodiment.

FIG. 20 is a diagram explaining feedback to user selection operation in the bike UI according to an embodiment.

FIG. 21 is a diagram explaining a case where the number of options increases or decreases according to a riding state in the bike UI according to an embodiment.

FIG. 22 is a diagram explaining another example of selection behavior while the user is riding the bike in the bike UI according to an embodiment.

FIG. 23 is a diagram explaining display examples of information according to recognition accuracy according to an embodiment.

FIG. 24 is a diagram explaining display examples of information according to recognition accuracy according to an embodiment.

FIG. 25 is a diagram explaining display examples in a case where limitation of the operation input mode is reported to the user according to an embodiment.

FIG. 26 is a diagram explaining display examples in a case where limitation of the input method is reported to the user according to an embodiment.

FIG. 27 is a diagram illustrating an example of a communication UI according to an embodiment.

FIG. 28 is a diagram illustrating an example of a communication UI according to an embodiment.

DESCRIPTION OF EMBODIMENTS

Hereinafter, embodiments of the present disclosure will be described in detail with reference to the appended drawings. In this specification and the appended drawings, structural elements that have substantially the same function and structure are denoted with the same reference numerals, and repeated explanation of these structural elements is omitted.

Further, description will be provided in the following order.
1. Outline of information processing apparatus according to an embodiment of the present disclosure
2. Configuration of information processing apparatus
3. Operation processing
3-1. Display control processing
3-2. User behavior recognition processing
3-3. Score acquisition processing
3-4. Input method selection processing
4. Display example
4-1. Bike UI
4-2. Communication UI
5. Conclusion

1. OUTLINE OF INFORMATION PROCESSING APPARATUS ACCORDING TO AN EMBODIMENT OF THE PRESENT DISCLOSURE

First, outline of an information processing apparatus according to an embodiment of the present disclosure will be described. FIG. 1 is a diagram explaining outline of an information processing apparatus 1 according to an embodiment. As illustrated in FIG. 1, the information processing apparatus 1 according to an embodiment is realized with, for example, a glasses-type head mounted display (HMD) mounted on the head of a user. A display unit 13 corresponding to lenses of the glasses located in front of eyes of the user when the user wears the information processing apparatus 1 may be a see-through type display unit or a non-see-through type display unit. The information processing apparatus 1 displays a display object at the display unit 13, thereby can present the display object ahead in the line of sight of the user. Further, the HMD which is one example of the information processing apparatus 1 is not limited to one which presents an image to both eyes, but may be one which displays an image only at one eye. For example, the HMD may be a one-eye type in which the display unit 13 which displays an image at one eye is provided.

Further, an outward camera 110 which shoots the line of sight direction of the user, that is, an external direction when the user wears the information processing apparatus 1 is provided at the information processing apparatus 1. Still further, although not illustrated in FIG. 1, various kinds of sensors such as an inward camera which shoots the eyes of the user when the user wears the information processing apparatus 1 and a microphone (hereinafter, referred to as a "mike") are provided at the information processing apparatus 1. There may be provided a plurality of outward cameras 110 and inward cameras. Note that when there are a plurality of outward cameras 110, it is possible to obtain a depth image (distance image) through parallax information, so that it is possible to sense the surrounding environment.

Note that the shape of the information processing apparatus 1 is not limited to the example illustrated in FIG. 1. For example, the information processing apparatus 1 may be an HMD of a head-band type (in which the information processing apparatus 1 is worn with a band running over the whole circumference of the head or with a band also running the top of the head as well as the side of the head) or an HMD of a helmet type (in which a visor portion of the helmet corresponds to a display). Further, the information processing apparatus 1 may be realized with a wearable apparatus such as a wristband type wearable apparatus (for example, a smart watch, including a case where there is a display or there is no display), a headphone type wearable apparatus (with no display) and a neckphone type wearable apparatus (which is worn around the neck, including a case where there is a display or there is no display).

Further, because the information processing apparatus 1 according to an embodiment is realized with the wearable apparatuses as described above and can be worn by the user, it is assumed that operation is input in various states such as when the user stops, as well as, when the user walks, when the user runs, and when the user rides a bike, or the like. Therefore, the information processing apparatus 1 includes various operation input capabilities such as sound input, gesture input using hand or head and input using the line of sight, in addition to buttons, switches (examples of operation members), or the like.

Here, there is a case where operability degrades because it is difficult to input operation with the same accuracy depending on a state of user behavior such as when the user stops and when the user moves. Further, when the user routinely wears a see-through type HMD (hereinafter, referred to as "smart eye glasses"), there is a risk that the user may not operate the HMD because it is difficult to input operation through the line of sight due to the afternoon sun, backlight, or the like.

Therefore, the information processing apparatus 1 according to an embodiment can further improve operability by preparing various operation input modes according to a state of user activity and dynamically switching the operation input mode according to the state of user activity.

The outline of the information processing apparatus 1 according to an embodiment has been described above. Subsequently, a configuration of the information processing apparatus 1 according to an embodiment will be described with reference to FIG. 2.

2. CONFIGURATION

FIG. 2 is a block diagram illustrating an example of the configuration of the information processing apparatus according to an embodiment. As illustrated in FIG. 2, the information processing apparatus 1 has a control unit 10, a sensor unit 11, an operation input unit 12, a display unit 13, a speaker 14, a communication unit 15 and a storage unit 16.
(Control Unit 10)

The control unit 10 which functions as an arithmetic processing unit and a control apparatus, controls the whole operation within the information processing apparatus 1 according to various kinds of programs. The control unit 10 is, for example, realized with electronic circuits such as a central processing unit (CPU) and a microprocessor. Further, the control unit 10 may include a read only memory (ROM) which stores a program, an operation parameter, or the like, to be used and a random access memory (RAM) which temporarily stores a parameter, or the like, which changes as appropriate.

Further, as illustrated in FIG. 2, the control unit 10 according to an embodiment functions as a recognition engine 100, a score acquiring unit 101, a behavior recognizing unit 102, an input method selecting unit 103, a display mode determining unit 104, a display information generating unit 105, a display control unit 106 and an operation input accepting unit 107.

The recognition engine 100 has a function of recognizing various kinds of states of the user or surrounding situations using various kinds of sensor information sensed by the sensor unit 11. More specifically, the recognition engine 100 includes a head posture recognition engine 100a, a depth recognition engine 100b, a simultaneous localization and mapping (SLAM) recognition engine 100c, a line of sight recognition engine 100d, a sound recognition engine 100e and a position recognition engine 100f. Note that the recognition engines illustrated in FIG. 1 are examples, and is not limited to this.

The head posture recognition engine 100a recognizes posture (orientation or tilt of the face with respect to the body) of the head of the user using various kinds of sensor information sensed by the sensor unit 11. For example, the head posture recognition engine 100a can recognize posture of the head of the user by analyzing at least any of a surrounding image shot by the outward camera 110, gyro information acquired by a gyro sensor 113, acceleration information acquired by an acceleration sensor 114 and orientation information acquired by an orientation sensor 115. Note that algorithm which is typically known may be used as algorithm for recognizing the posture of the head, and the algorithm is not particularly limited.

The depth recognition engine 100b recognizes depth information in space around the user using various kinds of sensor information sensed by the sensor unit 11. For example, the depth recognition engine 100b can recognize distance information of an object and a plan position of an object in surrounding space by analyzing a shot surrounding image acquired by the outward camera 111. Note that algorithm which is typically known may be used as algorithm for depth recognition, and the algorithm is not particularly limited.

The SLAM recognition engine 100c can identify the own position in surrounding space by estimating the own position and creating a map of the surrounding space at the same time using various kinds of sensor information sensed by the sensor unit 11. For example, the SLAM recognition engine 100c can identify the own position of the information processing apparatus 1 by analyzing a shot surrounding image acquired by the outward camera 110. Note that algorithm which is typically known may be used as algorithm for SLAM recognition, and the algorithm is not particularly limited.

Note that the recognition engine 100 can recognize space (grasp space) based on the above-described recognition result of the depth recognition engine 100b and the above-described recognition result of the SLAM recognition engine 100c. Specifically, the recognition engine 100 can recognize a position of the information processing apparatus 1 in surrounding three-dimensional space.

The line of sight recognition engine 100d detects the line of sight of the user using various kinds of sensor information sensed by the sensor unit 11. For example, the line of sight recognition engine 100d recognizes the line of sight direction of the user by analyzing a shot image of the eyes of the user acquired by the inward camera 111. Note that while algorithm for detecting the line of sight is not particularly limited, for example, the line of sight direction of the user can be recognized based on positional relationship between an inner corner of the eye and an iris or positional relationship between corneal reflex and a pupil.

The sound recognition engine 100e recognizes the user or environmental sound using various kinds of sensor information sensed by the sensor unit 11. For example, the sound recognition engine 100e can perform sound recognition, morphological analysis, recognition of a sound source, recognition of a noise level, or the like, by performing noise removal or sound source separation, or the like, on sound pickup information acquired by the microphone 112.

The position recognition engine 100f recognizes an absolute position of the information processing apparatus 1 using various kinds of sensor information sensed by the sensor unit 11. For example, the position recognition engine 100f recognizes the location of the information processing apparatus 1 (such as, for example, station, school, house, company, train and theme park) based on position information measured by a position measuring unit 116 and map information acquired in advance.

The score acquiring unit 101 can acquire a score indicating recognition accuracy of the recognition engine 100. For example, the score acquiring unit 101 calculates a score indicating accuracy of the recognition engine from a recognition result in each recognition engine of the recognition engine 100. Note that algorithm which is typically known may be used as algorithm for calculating a score, and the algorithm is not particularly limited.

The behavior recognizing unit 102 recognizes behavior of the user using various kinds of sensor information sensed by the sensor unit 11. For example, the behavior recognizing unit 102 recognizes a state of user behavior (an example of a state of activity) using at least any of an image shot by the outward camera 110, sound picked up by the microphone 112, angular velocity information of the gyro sensor 113, acceleration information of the acceleration sensor 114, orientation information of the orientation sensor 115 and absolute position information of the position measuring unit 116. As the state of user behavior, for example, a resting state, a walking state (walk slowly or jog), a running state (dash or run at high speed), a sitting state, a standing state, a sleeping state, a state where the user is riding a bike, a state where the user gets on a train, and a state where the user gets into a car can be recognized. Further, more specifically, the behavior recognizing unit 102 may recognize a state according to an amount of activity measured based on the angular velocity information and the acceleration information. Note that the above-described various kinds of sensor information according to an embodiment is one example of information regarding the state of user activity.

The input method selecting unit 103 selects an input method of the user operation for the information processing apparatus 1. The information processing apparatus 1 according to an embodiment has various input methods as described above. Specifically, for example, operation input modes can include operation input using the operation input unit 12 (such as buttons and switches), sound input, gesture input using hand or head, input using the line of sight and input which uses space recognition. The input which uses space recognition is an operation input mode which is triggered by, for example, movement of the user position to a predetermined position in space. An example of input which uses space recognition will be described with reference to FIG. 16.

In a state where operation can be input using various modes in this manner, the input method selecting unit 103 selects an optimal operation input mode according to a current state. Selection of the operation input mode is not limited to selection of an optimal operation input mode, and may be selection of a plurality of operation input modes. When a plurality of operation input modes are selected, the input method selecting unit 103 may select the operation input modes according to priority.

Further, the input method selecting unit 103 dynamically selects the operation input mode according to a state. For example, the following criteria are assumed as a criterion for selecting the operation input mode. That is, the input method selecting unit 103 may select the operation input mode according to a "state of user behavior" recognized by the behavior recognizing unit 102 or a "score (an accuracy score of the recognition engine, that is, recognition accuracy)" acquired by the score acquiring unit 101, or may select the operation input mode while taking into account both the state of user behavior and the recognition accuracy.

For example, when the state of user behavior (which is one example of a state of activity, such as, for example, a resting state, a walking state and a running state) is a first state, the input method selecting unit 103 selects first operation (input mode) for causing an operation target to operate in the first operation, and, when the state of user behavior is a second state, the input method selecting unit 103 selects a second operation input mode for causing the operation target to operate in the second operation input mode which is different from the first operation. By this, it is possible to prevent erroneous operation or a risk, and automatically select an operation input mode which can cause the operation target to operate more easily.

Further, as the recognition accuracy, accuracy of the sound recognition engine 100e to be used for sound input, the head posture recognition engine 100a to be used for head gesture input, the line of sight recognition engine 100d to be used for input using the line of sight, the depth recognition engine 100b to be used for space recognition and the SLAM recognition engine 100c is assumed. By selecting the operation input mode while taking into account the recognition accuracy, it is possible to prevent erroneous input due to low recognition accuracy or a risk that recognition may not be performed and thus operation may not be accepted, and it is possible to automatically select an operation input mode with higher operability.

Here, selection of the operation input mode will be specifically described with reference to FIG. 3 to FIG. 7. FIG. 3 to FIG. 7 illustrate recognition engines (that is, available modal) to be used in the operation input mode selected according to a state.

FIG. 3 is a diagram explaining a case where the operation input mode is switched according to the recognition accuracy according to an embodiment. Here, as an example, a vertical axis indicates accuracy of the recognition engine (specifically, for example, SLAM recognition, depth recognition, and also collectively referred to as "image recognition") which performs recognition by analyzing a shot image acquired from the outward camera 110, and a horizontal axis indicates a state of user behavior (for example, an amount of activity).

As illustrated in FIG. 3, in the case of a region where accuracy of image recognition is the lowest, it is highly likely that the operation input mode which uses space recognition based on a result of the image recognition may not be used (space recognition does not correctly function). Therefore, the input method selecting unit 103 may select any of head gesture input which uses head posture recognition based on sensor information of the gyro sensor 113, the acceleration sensor 114, or the like, and input using the line of sight which uses line of sight recognition based on an image shot by the inward camera 111. Note that, when the inward camera 111 may not correctly acquire the line of sight from an image of the eyes of the user due to the afternoon sun (when accuracy of recognition of the line of sight is low), the input method selecting unit 103 may select only the head gesture input.

Subsequently, in the case of a region where the accuracy of image recognition is the second lowest, as illustrated in FIG. 3, the input method selecting unit 103 may select head gesture input which uses head posture recognition and input using the line of sight which uses line of sight recognition. The user can input operation using either mode.

Subsequently, when the accuracy of image recognition is medium, as illustrated in FIG. 3, the input method selecting unit 103 may select input which uses space recognition and head gesture input which uses head posture recognition.

Subsequently, when the accuracy of image recognition is higher than medium, as illustrated in FIG. 3, the input method selecting unit 103 may select input which uses space recognition and input using the line of sight which uses line of sight recognition.

Then, when the accuracy of image recognition is high, as illustrated in FIG. 3, the input method selecting unit 103 may select input which uses space recognition, input using the line of sight which uses line of sight recognition, head gesture which uses head posture recognition and sound input which uses sound recognition. As the recognition accuracy is higher, input can be performed using a more variety of operation input modes.

Note that, when the user runs at high speed (for example, when the user is running or is riding a bike), (or when an amount of activity is high, for example, when the user shakes his/her head quickly), in order to prevent erroneous operation, the information processing apparatus 1 does not select any operation input mode and turns off the operation, so that only display of the display object and information acquisition by the sensor unit 11 are performed.

In this manner, by dynamically changing the input mode while taking into account, for example, accuracy of image recognition, it is possible to provide an operation input mode with high operability to the user. Further, when none of the recognition engines can be used because accuracy of all the recognition engines is low, the control unit 10 of the information processing apparatus 1 displays an icon indicating that operation may not be currently accepted at the display unit 13 or output sound indicating that operation may not be currently accepted from the speaker 14.

FIG. 4 is a diagram explaining a case where the operation input mode is switched according to a state of user behavior according to an embodiment. The state of user behavior can be recognized by the behavior recognizing unit 102 based on, for example, the amount of activity acquired from the acceleration information detected by the acceleration sensor 114. Further, the recognition accuracy on the vertical axis illustrated in FIG. 4 indicates, for example, accuracy of image recognition as in FIG. 3.

As illustrated in FIG. 4, according to the state of user behavior, for example, a "resting state", a "walking state (slow to quick)" and a "running state (slow to quick)", input which uses space recognition, input using the line of sight which uses line of sight recognition, head gesture which uses head posture recognition and sound input which uses sound recognition are respectively selected. In the example illustrated in FIG. 4, as the amount of activity is lower, input can be performed using a more variety of input methods. For example, as illustrated in FIG. 4, in the case of the resting state, input which uses space recognition, input using the line of sight which uses line of sight recognition, head gesture which uses head posture recognition and sound input which uses sound recognition are selected. Subsequently, when the user walks slowly, input which uses space recognition and input using the line of sight which uses line of sight recognition are selected. Then, when the user walks quickly, input using the line of sight which uses line of sight recognition and head gesture which uses head posture recognition are selected. Then, when the user runs slowly, only head gesture which uses head posture recognition or only input using the line of sight which uses line of sight recognition is selected. Further, when the user runs at high speed (that is, when the amount of activity is high), the information processing apparatus 1 does not select any operation input mode and turns off the operation, so that only display of the display object and information acquisition by the sensor unit 11 are performed, to prevent erroneous operation.

FIG. 5 is a diagram explaining a case where the input method is switched according to recognition accuracy and a state of user behavior according to an embodiment. In the example illustrated in FIG. 5, as the amount of activity is lower and recognition accuracy is higher, input can be performed using a more variety of operation input modes. Further, when the amount of activity is high and recognition accuracy is low, the information processing apparatus 1 does not select any operation input mode and turns off the operation to prevent erroneous operation.

While selection of the input method described above has been described using a case where the selection criterion is based on two axes, an embodiment is not limited to this, and, for example, the selection criterion may be based on one axis. This will be described below with reference to FIG. 6 and FIG. 7.

FIG. 6 is a diagram explaining a case where the operation input mode is switched according to a walking state according to an embodiment. In the example illustrated in FIG. 6, as a level of the walking state is lower, that is, the amount of activity is lower, input can be performed using a more variety of operation input modes. Here, the walking state is recognized according to, for example, the amount of activity, and, when the amount of activity is sufficiently low, it can be recognized as "sit down", when the amount of activity is low, it can be recognized as "stand up", when the amount of activity is medium, it can be recognized as "walk slowly", when the amount of activity is higher than medium, it can be recognized as "jog", and when the amount of activity is sufficiently high, it can be recognized as "dash". In the case of "dash" when the level of the walking state is sufficiently high, the information processing apparatus 1 does not select any operation input mode and turns off the operation (so that the state is put into a state where no operation input is accepted) to prevent erroneous operation.

FIG. 7 is a diagram explaining a case where the operation input mode is switched according to a bike riding state according to an embodiment. That is, FIG. 7 illustrates switching of the operation input mode when the user rides the bike while wearing the information processing apparatus 1. In the example illustrated in FIG. 7, as the level of riding state is lower, that is, the amount of activity is lower, input can be performed using a more variety of input methods. Here, the riding state of the bike is recognized by, for example, the amount of activity, and, when the amount of activity is low, it can be recognized as "stop" or "ride at low speed", when the amount of activity is medium, it can be recognized as "ride at medium speed", when the amount of activity is high, it can be recognized as "ride at high speed", and when the amount of activity is further high, "dancing or in a curve". Further, in the case of "dancing or in a curve" when the level of the riding state is high, the information processing apparatus 1 does not select any operation input mode and turns off the operation to prevent erroneous operation.

In the example described above, while an example where the operation input mode to be selected is switched based on either or both of the recognition accuracy and the state of user behavior, an embodiment is not limited to this, and the operation input mode may be switched by being triggered by other factors such as change of the environment and states of other devices. For example, the operation input mode may be selected according to a trigger (such as, for example, a gazing point of the line of sight, biological information, feeling, posture and position (location)) which "depends on the user". Further, the operation input mode may be selected according to a trigger (such as a display size, a display position, a display animation mode, attribute of content (a type, a degree of importance, priority or an application type), resolution and color of the display object) which "depends on content". Still further, the operation input mode may be selected according to a trigger (such as background (scenery of a field of view), illuminance, location (outdoor, indoor, situation), behavior history (whether or not the user is familiar with the location), a surrounding situation (whether or not there are cars of others, density), time, a direction of the wind and an air volume) which "depends on the environment". Further, the operation input mode may be selected according to a trigger (such as device attribute (a wristband, an HMD, a TV, a smartphone), a remaining battery amount, battery capacity, processing load of the CPU, a CPU temperature, a state where a wearable device is worn (worn, not worn, a location where the device is worn)) which "depends on the device".

The display mode determining unit 104 determines a display mode (representation method) corresponding to the operation input mode selected by the input method selecting unit 103. For example, when the first operation input mode is selected, the display mode determining unit 104 determines a first display mode, and, when the second operation input mode is selected, the display mode determining unit 104 determines a second display mode which is different from the first display mode. For example, when the "operation input mode which uses space recognition" is selected by the input method selecting unit 103, the display mode determining unit 104 determines a representation method which enables use of the operation input mode which uses space recognition, and, when input using the line of sight is selected, the display mode determining unit 104 determines a representation method which enables use of the input using the line of sight. Further, when head gesture input is selected, the display mode determining unit 104 determines a representation method which enables use of the head gesture input.

Further, when a plurality of operation input modes are selected by the input method selecting unit 103, the display mode determining unit 104 may determine a display mode corresponding to an operation input mode with the highest priority. For example, the operation input mode is set such that input which uses space recognition has the highest priority, input using the line of sight has the second highest priority, head gesture has the third highest priority, and sound input is the fourth highest priority.

The display information generating unit 105 generates a display object (also referred to as a "display image") to be displayed at the display unit 13. Further, the display information generating unit 105 according to an embodiment generates a display image according to the display mode determined by the display mode determining unit 104. For example, the display information generating unit 105 generates information for displaying a selection target (option) which is one example of the display image in the display mode determined by the display mode determining unit 104.

The display control unit 106 performs control to output the display information generated by the display information generating unit 105 from the display unit 13. For example, the display control unit 106 performs control to display (display in front of the user) a selection target (display object) of the display mode corresponding to the selected operation input mode, generated by the display information generating unit 105 at the display 13.

The operation input accepting unit 107 accepts operation input from the user and outputs operation input information to the display information generating unit 105 (or the control unit 10). The operation input accepting unit 107 according to an embodiment accepts operation input using one or more operation input modes selected by the input method selecting unit 103. That is, information used by the operation input accepting unit 107 to accept user operation input differs according to the operation input mode selected by the input method selecting unit 103. For example, when "head gesture" and "input using the line of sight" are selected by the input method selecting unit 103, gyro sensor information, acceleration information, orientation information, and information on an image shot by the inward camera 111 are used. Further, when "input which uses space recognition" is selected by the input method selecting unit 103, information on an image shot by the outward camera 110 is used.

(Sensor Unit 11)

The sensor unit 11 has a function of acquiring various kinds of information relating to the user or the surrounding environment. For example, the sensor unit 11 includes the outward camera 110, the inward camera 111, the microphone 112, the gyro sensor 113, the acceleration sensor 114, the orientation sensor 115 and the position measuring unit 116. Note that specific examples of the sensor unit 11 described here are examples, and is not limited to these. Further, there may be provided a plurality of sensors as each of the sensors.

The outward camera 110 and the inward camera 111 each has a lens system constituted with an imaging lens, a diaphragm, a zoom lens, a focus lens, or the like, a driving system which causes the lens system to perform focus operation or zoom operation, a solid-state imaging element array which performs photoelectric conversion on imaging light obtained by the lens system to generate an imaging signal, or the like. The solid-state imaging element array may be realized with, for example, a charge coupled device (CCD) sensor array, or a complementary metal oxide semiconductor (CMOS) sensor array.

The microphone 112 picks up sound of the user or surrounding environmental sound and outputs the sound to the control unit 10 as sound data.

The gyro sensor 113, which is realized with, for example, a triaxial gyro sensor, detects angular velocity (rotation speed).

The acceleration sensor 114, which is realized with, for example, a triaxial acceleration sensor (also referred to as a "G sensor"), detects acceleration upon traveling.

The orientation sensor 115, which is realized with, for example, a triaxial geomagnetic sensor (compass), detects an absolute direction (orientation).

The position measuring unit 116 has a function of detecting a current position of the information processing apparatus 1 based on a signal acquired from outside. Specifically, for example, the position measuring unit 116, which is realized with a global positioning system (GPS) measuring unit, receives a radio wave from a GPS satellite, detects a position where the information processing apparatus 1 exists, and outputs the detected position information to the control unit 10. Further, the position measuring unit 116 may detect the position through transmission/reception with, for example, Wi-Fi (registered trademark), Bluetooth (registered trademark), a mobile phone, a PHS, a smartphone, or the like, or through near field communication, or the like, other than GPS.

(Operation Input Unit 12)

The operation input unit 12 is realized with an operation member having a physical structure such as a switch, a button and a lever.

(Display Unit 13)

The display unit 13 is realized with a lens unit (one example of the transmission type display unit) which performs display using, for example, a hologram optical technique, a liquid crystal display (LCD) apparatus, an organic light emitting diode (OLED) apparatus, or the like. Further, the display unit 13 may be a transmissive, a semi-transmissive or a non-transmissive unit.

(Speaker 14)

The speaker 14 reproduces a sound signal according to control by the control unit 10.

(Communication Unit 15)

The communication unit 15 is a communication module for transmitting/receiving data to/from other apparatuses in a wired/wireless manner. The communication unit 15 performs wireless communication with external equipment directly or through a network access point using a method such as, for example, a wired local area network (LAN), a wireless LAN, wireless fidelity (Wi-Fi, registered trademark), infrared communication, Bluetooth (registered trademark) and near field/non-contact communication.

(Storage Unit 16)

The storage unit 16 stores a program and a parameter for the above-described control unit 10 to execute each function. For example, in the storage unit 16, various kinds of thresholds to be used for user behavior recognition processing to be performed by the behavior recognizing unit 102, recognition algorithm, algorithm for calculating a recognition accuracy score, various kinds of thresholds to be used for input method selection processing, or the like, are stored.

While the configuration of the information processing apparatus 1 according to an embodiment has been specifically described above, the configuration of the information processing apparatus 1 according to an embodiment is not limited to the example illustrated in FIG. 2. For example, at least part of processing of the control unit 10 of the information processing apparatus 1 may be performed at a server in the cloud to which the information processing apparatus 1 is connected through the communication unit 15.

3. OPERATION PROCESSING

Subsequently, operation processing of the information processing apparatus 1 according to an embodiment will be specifically described with reference to FIG. 8 to FIG. 12.

<3-1. Display Control Processing>

FIG. 8 is a flowchart illustrating display control processing according to an embodiment. As illustrated in FIG. 8, first, the control unit 10 of the information processing apparatus 1 acquires sensor information from the sensor unit 11 (step S103).

Then, the behavior recognizing unit 102 recognizes a user behavior state based on the acquired sensor information (step S106). The user behavior recognition processing will be described in detail later with reference to FIG. 9.

Meanwhile, the score acquiring unit 101 acquires (calculates) an accuracy score from a processing result of the recognition engine 100 based on the acquired sensor information (step S109). The score acquisition processing will be described in detail later with reference to FIG. 10.

Then, the input method selecting unit 103 selects the operation input mode (that is, determines a recognition engine to be used) based on the result of user behavior recognition (that is, the user behavior state) and the recognition accuracy score (step S112). The input method selection processing will be described in detail later with reference to FIG. 11 and FIG. 12. Further, in the example illustrated in FIG. 8, while the operation input mode is selected based on the user behavior state and the recognition accuracy score, an embodiment is not limited to this, and the operation input mode may be selected based on at least one of them or using other triggers described above.

Then, the display mode determining unit 104 determines a display mode according to the operation input mode selected by the input method selecting unit 103 (step S115).

Then, the display information generating unit 105 generates display information (UI drawing processing) according to the determined display mode (step S118), and, thus, the generated display information is displayed at the display unit 13 by the display control unit 106 (step S121).

The above-described acquisition of sensor information (step S103), recognition of the user behavior state (step S106) and acquisition of the recognition accuracy score (step S109) are performed continuously, and, when there is change in the user behavior state or the score (step S124/Yes), the operation input mode is reselected (step S112). By this, because different operation input modes are selected according to change of the state, for example, change of a state from a state where the user is walking, to a state where the user gets on a bike, and further to a state where the user rides a bike, the same options can be displayed through a display mode which is different according to the operation input mode. An example of change of the display mode of the options according to the behavior state will be described later with reference to FIG. 18.

The above-described steps S103 to S124 are repeated until the display processing (UI drawing processing) is finished (step S127).

<3-2. User Behavior Recognition Processing>

An example of the user behavior state recognition processing described in the above-described step S106 will be specifically described next with reference to FIG. 9. FIG. 9 is a flowchart illustrating the user behavior recognition processing according to an embodiment.

As illustrated in FIG. 9, first, the behavior recognizing unit 102 measures an amount of user activity based on the sensor information acquired by the sensor unit 11, specifically, for example, the acceleration information (step S130).

Subsequently, when the measured amount of activity is lower than a threshold Th1 (step S133/Yes), the behavior recognizing unit 102 recognizes the state as a resting state (step S136).

Then, when the measured amount of activity is higher than the threshold Th1 and lower than a threshold Th2 (step S139/Yes), the behavior recognizing unit 102 recognizes the state as a slow walking state (step S142).

Then, when the measured amount of activity is higher than the threshold Th2 and lower than a threshold Th3 (step S145/Yes), the behavior recognizing unit 102 recognizes the state as a quick walking or jogging state (step S148).

Further, when the measured amount of activity is higher than the threshold Th3 (step S151/Yes), the behavior recognizing unit 102 recognizes the state as a running state (step S154).

A case has been described above where the user behavior state recognition processing is performed based on the amount of activity. Note that the user behavior state recognition processing according to an embodiment is not limited to the case where the processing is performed based on the amount of activity, and the state can be recognized as a walking state, a running state or a bike riding state based on, for example, position information, according to whether the user travels on a road or a sidewalk.

<3-3. Score Acquisition Processing>

An example of the recognition accuracy score acquisition processing described in the above-described step S109 will be specifically described next with reference to FIG. 10. FIG. 10 is a flowchart illustrating the score acquisition processing according to an embodiment.

As illustrated in FIG. 10, first, the head posture recognition engine 100a recognizes head posture based on sensor information acquired by at least one of the gyro sensor 113 and the acceleration sensor 114 and sensor information acquired by the orientation sensor 115 (step S160).

Then, the score acquiring unit 101 acquires (calculates) a score indicating accuracy of a recognition processing result by the head posture recognition engine 100a (step S163).

Further, when the depth recognition engine 100b performs depth recognition based on the image shot by the outward camera 110 (step S166), the score acquiring unit 101 acquires (calculates) a score indicating accuracy of a recognition processing result by the depth recognition engine 100b (step S169).

Further, when the SLAM recognition engine 100c performs SLAM recognition based on the image shot by the outward camera 110 (step S172), the score acquiring unit 101 acquires (calculates) a score indicating accuracy of a recognition processing result by the SLAM recognition engine 100c (step S175).

Still further, when the line of sight recognition engine 100d performs line of sight recognition based on the image shot by the inward camera 111 (step S178), the score acquiring unit 101 acquires (calculates) a score indicating accuracy of a recognition processing result by the line of sight recognition engine 100d (step S181).

Further, when the sound recognition engine 100e performs sound recognition based on sound pickup information of the microphone 112 (step S184), the score acquiring unit 101 acquires (calculates) a score indicating accuracy of a recognition processing result by the sound recognition engine 100e (step S187).

<3-4. Input Method Selection Processing>

An example of the input method selection processing described in the above-described step S112 will be specifically described next with reference to FIG. 11. FIG. 11 is a flowchart illustrating the input method selection processing according to an embodiment.

As illustrated in FIG. 11, first, the input method selecting unit 103 selects an available operation input mode based on the recognized user behavior state (step S200). For example, when the state is a resting state (step S136 illustrated in FIG. 9), the input method selecting unit 103 may select any of "input which uses space recognition, input using the line of sight and head gesture input", "sound input", "gesture input using hand", and "input using a button or a switch". Further, when the state is a slow walking state (step S142 illustrated in FIG. 9), the input method selecting unit 103 may select any of "input using the line of sight and head gesture input", "sound input", "gesture input using hand" and "input using a button or a switch". Further, when the state is a quick walking or jogging state (step S148 illustrated in FIG. 9), the input method selecting unit 103 may select any of "input using the line of sight", "sound input", "gesture input using hand" and "input using a button or a switch". Still further, when the state is a running state (step S154 illustrated in FIG. 9), the input method selecting unit 103 does not select any operation input mode and puts the state into a state where operation may not be performed, so that only display of information and output of sound are performed.

Further, the input method selecting unit 103 selects an available operation input mode based on the accuracy score of the recognition engine (step S203). This selection will be described later with reference to FIG. 12.

Then, the input method selecting unit 103 selects an available operation input mode while taking into account the above-described each selection result (step S206).

FIG. 12 is a flowchart illustrating the input method selection processing based on the recognition accuracy score according to an embodiment. As illustrated in FIG. 12, first, when the score of the head posture recognition engine 100a exceeds a predetermined threshold Th10 (step S230/Yes), the input method selecting unit 103 turns on a utilization flag of the operation input mode which uses head posture recognition (step S233).

On the other hand, when the score of the head posture recognition engine 100a does not exceed the predetermined threshold Th10 (step S230/No), the input method selecting unit 103 turns off the utilization flag of the operation input mode which uses head posture recognition (step S236).

Subsequently, when the score of the depth recognition engine 100b exceeds a predetermined threshold Th11 (step S239/Yes), the input method selecting unit 103 turns on a utilization flag of the operation input mode which uses depth recognition (step S242).

On the other hand, when the score of the depth recognition engine 100b does not exceed the predetermined threshold Th11 (step S239/No), the input method selecting unit 103 turns off the utilization flag of the operation input mode which uses depth recognition (step S245).

Subsequently, when the score of the SLAM recognition engine 100c exceeds a predetermined threshold Th12 (step S248/Yes), the input method selecting unit 103 turns on a utilization flag of the operation input mode which uses SLAM recognition (step S251).

On the other hand, when the score of the SLAM recognition engine 100c does not exceed the predetermined threshold Th12 (step S248/No), the input method selecting unit 103 turns off the utilization flag of the operation input mode which uses SLAM recognition (step S254).

Subsequently, when the score of the line of sight recognition engine 100d exceeds a predetermined threshold Th13 (step S257/Yes), the input method selecting unit 103 turns on a utilization flag of the operation input mode which uses line of sight recognition (step S260).

On the other hand, when the score of the line of sight recognition engine 100d does not exceed the predetermined threshold Th13 (step S257/No), the input method selecting unit 103 turns off the utilization flag of the operation input mode which uses line of sight recognition (step S263).

Subsequently, when the score of the sound recognition engine 100e exceeds a predetermined threshold Th14 (step S266/Yes), the input method selecting unit 103 turns on a utilization flag of the operation input mode which uses sound recognition (step S269).

On the other hand, when the score of the sound recognition engine 100e does not exceed the predetermined threshold Th14 (step S266/No), the input method selecting unit 103 turns off the utilization flag of the operation input mode which uses sound recognition (step S272).

In this manner, the input method selecting unit 103 can select the operation input mode according to the recognition accuracy according to whether a utilization flag of each operation input mode is turned on or off, determined based on the accuracy score.

4. DISPLAY EXAMPLE

Subsequently, a display example according to an embodiment will be specifically described with reference to FIG. 13 to FIG. 28. The information processing apparatus 1 according to an embodiment is realized with, for example, a transmissive HMD as illustrated in FIG. 1, that is, smart eye glasses, and can display (augmented reality (AR) display)

display information at the display unit 13 (corresponding to a lens unit) located in front of the eyes of the user while the display information is superimposed on the scenery in real space when the user wears the information processing apparatus 1. In the present specification, AR display is to perform display so that an observer can perceive a virtual object as if the virtual object were a real object existing in real space. The information processing apparatus 1 can change display of the virtual object based on a sensing result of real space around the observer. For example, the information processing apparatus 1 can sense an ID, a position or posture of a real object existing in a region viewed by the observer, and can display the virtual object as if the virtual object were attached to the real object by changing display of the virtual object so as to correspond to the sensing result. Further, the information processing apparatus 1 can change representation of the virtual object based on a sensing result of visual conditions (such as a viewpoint, the line of sight, a field of view, a focal point and posture of the head) of the observer in the case of an optical see-through type display unit, or a sensing result of shooting conditions (such as a camera position, posture, a focal point and a shooting range) of a camera in the case of a video see-through type display unit. For example, it is controlled such that the virtual object is displayed larger as the user approaches the virtual object, and, when the viewpoint moves around the virtual point, the virtual point is displayed while being rotated in accordance with motion of the viewpoint. Further, for example, sports, a game, recreation or communication is assumed as a scene where the information processing apparatus 1 according to an embodiment is utilized, and, when the user plays sports, or the like, various related information is presented. Further, because it is possible to input operation through input which uses space recognition, sound input, head gesture or input using the line of sight, the user can input operation without using his/her hands. Further, the information processing apparatus 1 according to an embodiment can further improve user friendliness by automatically switching the operation input mode to a natural input mode according to a user behavior state.

<4-1. Bike UI>

First, as an example, various display examples where the user utilizes a bike while wearing the information processing apparatus 1 illustrated in FIG. 1 will be specifically described with reference to FIG. 13 to FIG. 26.

FIG. 13 is a diagram illustrating a display example of a bike UI before the user gets on a bike according to an embodiment. When the information processing apparatus 1 detects that the user approaches the bike through behavior recognition, as illustrated in FIG. 13, related information (such as a today's accumulative riding distance, air pressures of tires and display of a key) and a pacemaker 30 (image) are displayed around the bike 20 (real object) of the user. In this case, the information processing apparatus 1 accepts selection of the bike 20 through recognition of natural behavior (space recognition) that the user approaches the bike 20 to get on his/her bike 20. Decision of selection of the bike 20 can be fed back by, for example, performing display control to encourage the user to unlock a key mark of the bike 20 illustrated in FIG. 15. Further, the bike 20 of the user may be detected through, for example, pattern matching between an analysis result (object extraction) of an image shot by the outward camera 110 and an image of the bike of the user registered in advance, or may be detected through beacon reception from a communication apparatus provided at the bike.

FIG. 14 is a diagram illustrating a display example of the bike UI when the user gets on the bike according to an embodiment. When the user gets on the bike, carefully selected options of menu are displayed at the bike. In the example illustrated in FIG. 14, two options 32 and 33 of navigation and training are displayed above a handle bar 21. In this case, for example, the information processing apparatus 1 accepts menu selection through, for example, natural action (line of sight recognition) that the user sees menu which the user desires to utilize.

FIG. 15 illustrates a display example of the bike UI when the user rides the bike according to an embodiment. When the user selects "training", as illustrated in FIG. 15, the pacemaker 30 (image) is displayed in front of the user. The user can train by riding the bike while following the pacemaker 30. The control unit 10 of the information processing apparatus 1 continuously adjusts a virtual display position (distance with the user in space) of the pacemaker 30 with respect to the user based on predetermined speed (target speed, pace) of the pacemaker 30 and the user speed. The user can reach the finish line by riding the bike while following the pacemaker 30 as illustrated in FIG. 16. Further, a user state during riding can be recognized by user traveling (space recognition) or whether user sees the pacemaker 30 (line of sight recognition). When the user does not follow the pacemaker 30 or does not see the pacemaker 30, for example, as illustrated in FIG. 17, display control may be performed such that the pacemaker 30 stops and turns toward the user. By this, when the user does not see or follow the pacemaker 30, it is possible to prevent the pacemaker 30 from disappearing from the field of view of the user at the own speed (target speed, pace). When the user sees the pacemaker 30 or starts riding again, the pacemaker 30 also starts riding again and training is continued. Further, as illustrated in FIG. 17, the user can be notified that application correctly runs by the pacemaker 30 stopping according to the user behavior.

Subsequently, switching of the operation input mode according to the user behavior state in the bike UI will be described with reference to FIG. 18. FIG. 18 is a diagram explaining switching of the operation input mode according to the user behavior state in the bike UI according to an embodiment. Switching of the operation input mode according to an embodiment can be accordingly regarded as switching of a display mode of options.

As illustrated in FIG. 18, the operation input mode is switched, and a display mode of options changes according to a level of riding state (an amount of activity). Specifically, for example, in the case of a stopping state, "input using the line of sight" and "gesture input using hand" are selected, and a navigation option 32 and a training option 33 are displayed in a three-dimensional manner over the handle bar 21. By this, the user is encouraged to perform natural behavior (operation input), for example, sees an option which the user desires to select or puts his/her hand over a three dimensional display of an option which the user desires to select.

Further, in the case of riding at low speed or riding at medium speed, "input which uses space recognition" is selected, and the training pacemaker 30 and the navigation pacemaker 31 are displayed in front of the user as options (display objects). The user can select an option by actually riding a bike (selection behavior) so as to follow the pacemaker which the user desires to select. Here, user selection behavior will be specifically described with reference to FIG. 19.

FIG. 19 is a diagram explaining selection behavior of the user in the bike UI according to an embodiment. First, as illustrated in an upper part of FIG. 19, the training pacemaker 30 and the navigation pacemaker 31 are displayed as options in front of the user who gets on the bike. Then, as illustrated in a middle part of FIG. 19, the pacemakers 30 and 31 displayed in front of the user start riding, and the user steers the handle to a direction of the pacemaker which the user desires to select. Then, as illustrated in a lower part of FIG. 19, when the user actually follows the pacemaker 30 which the user desires to select, the pacemaker 31 moves backward, so that it is possible to select the pacemaker 30 (training). Such selection behavior of the user can be recognized by, for example, space recognition processing which uses recognition results of the depth recognition engine 100b and the SLAM recognition engine 100c. Note that the displayed pacemakers may be a life-size pacemaker or may be simple text display. Further, when the pacemakers are displayed in front of the user as options, operation input is not limited to selection behavior of the user, but may be accepted using other selected operation input modes such as input using the line of sight (fixing his/her eyes on the pacemaker which the user desires to select) and head gesture (turning his/her face to the pacemaker which the user desires to select).

Further, as feedback of selection operation with respect to the pacemakers (options) displayed in front of the user, for example, as illustrated in FIG. 20, feedback of selection operation of the user can be realized by performing display control so that the selected pacemaker 30 is made to turn around. It is also possible to make the feedback of the selection operation different depending on the selected operation input modes (such as input which uses space recognition, input using the line of sight, and head gesture).

Subsequently, returning to FIG. 18, when the user rides the bike at high speed, dancing or is in the curve, in order to prevent erroneous operation, it is also possible to perform setting such that no option is provided (selection operation is not accepted, operation is turned off).

In this manner, in an embodiment, even the same options (here, as an example, selection of training and navigation) are displayed at different display modes according to the user behavior state (for example, when the user stops, or when the user rides the bike).

Subsequently, another example of change of the display mode of options according to a riding state will be described with reference to FIG. 21. FIG. 21 is a diagram explaining a case where the number of options increases or decreases according to a riding state. As illustrated in FIG. 21, for example, when the user stops, N options (for example, three options 34a, 34b and 34c) may be displayed, and, when the user rides at low speed or medium speed, N−1 options (for example, two options 34a and 34b) may be displayed. Because, in the case of low-speed riding to medium-speed riding, it is assumed that it is difficult to see options compared to the case when the user stops, by reducing the number of options, user's burden is reduced. Further, in the case of low-speed riding to medium-speed riding, by displaying the options at a wider display interval, it is possible to avoid erroneous operation in selection or difficulty of operation. Further, as illustrated in FIG. 21, when the user rides at high speed, dancing or is in the curve, in order to prevent erroneous operation, it is also possible to perform setting such that no option is provided (selection operation is not accepted, operation is turned off).

In this manner, in an embodiment, it is possible to increase or decrease the options according to the user behavior state.

Another example of selection behavior while the user is riding the bike will be described next with reference to FIG. 22. FIG. 22 is a diagram explaining another example of selection behavior according to an embodiment. As illustrated in FIG. 22, for example, while the user is riding the bike, options 35 and 36 may be displayed on the road ahead of the user. The options 35 and 36 respectively include arrows and icons of corresponding application. The user can select the option by riding the bike on the option (icon) while following the arrow displayed on the road. The information processing apparatus 1 can recognize that the user rides on the option which is AR displayed through space recognition.

Further, the UI illustrated in FIG. 22 may be displayed, for example, after the user reaches the destination. For example, when the options 35 and 36 respectively correspond to social communication, social communication (such as, for example, email, blog, a microblogging site, an image posting site, and an electronic bulletin board) indicated with the selected icon is activated, and user riding information is posted on the web site of the social communication. Further, when the option corresponding to data storage is selected, the riding information (such as training data) can be stored. In this manner, it is possible to perform selection operation through natural behavior that the user rides the bike without performing explicit operation such as operation on a screen. Further, because information (including options) is displayed in line with a real object such as on the road, it is possible to see the information and the real object at the same time, so that it is possible to confirm the UI with low load.

Subsequently, a case where an information display method is switched according to recognition accuracy will be described with reference to FIG. 23 and FIG. 24. FIG. 23 and FIG. 24 are diagrams explaining an information display example according to recognition accuracy.

A left part of FIG. 23 illustrates a display example in the case where space recognition accuracy is low or where space recognition may not be performed. In this case, for example, an information image 40 including information such as real-time speed, average speed, maximum speed, current date and time, time (training time), a distance and a heart rate is displayed at a determined position in front of the eyes of the user, for example, 1.5 meters ahead of the eyes for a certain period of time. The display illustrated in the left part of FIG. 23 is non-AR display, and the information image 40 is localized with respect to the display (in other words, the information image 40 is not localized with respect to space to be recognized or an object existing in the space). On the other hand, a right part of FIG. 23 illustrates a display example in the case where space recognition accuracy is high. In this case, for example, an information image 41 indicating real-time speed is AR displayed on the road ahead of the user. That is, for example, the information image 41 is displayed, while, for example, being fixed on the road (localized with respect to a real object of "road"), and disappears from the field of view when the user passes the information image 41.

A left part of FIG. 24 illustrates a display example in the case where space recognition accuracy is low and space recognition can be performed only around the user (near side). In this case, for example, an information image 42 including information relating to speed, or the like, is localized with respect to a real object recognized around the user, for example, the handle bar 21, and displayed (AR displayed) over the handle bar 21 for a certain period of time. On the other hand, a right part of FIG. 24 illustrates a display example in the case where space recognition accuracy is high. In this case, for example, an information image 43 indicating name of the person who rides in front of the user, a real-time heart rate, the number of rotations, or the like, is displayed (AR displayed) in association with (while being localized to) the person (real object). Note that the information images 40, 41, 42 and 43 illustrated in FIG. 23 and FIG. 24 may be represented in, so-called, a two-dimensional (non-stereoscopic) manner, or in a three-dimensional (stereoscopic) manner.

A display example in the case where the user is notified of limitation of the operation input mode will be described next with reference to FIG. 25 and FIG. 26. As illustrated in FIG. 25, for example, when input which uses space recognition may not be performed, notification display 45 with text indicating that "space recognition unavailable" is displayed in front of the user. Further, when input which uses sound recognition may not be performed, notification display 46 in which a nix sign is overlapped on an icon of a microphone is displayed in front of the user. Further, when a plurality of operation input modes may not be used, for example, when input which uses sound recognition and input which uses line of sight recognition may not be used, the above-described notification display 46 and notification display 47 in which a nix sign is overlapped on an icon of eyes may be displayed in front of the user.

Further, as illustrated in FIG. 26, it is also possible to notify the user of unavailable operation input mode with sound or text using a virtual display character such as the pacemaker 30 which rides ahead of the user. In the example illustrated in the left part of FIG. 26, notification display 48 in which the pacemaker 30 communicates with the user with text that "sound recognition will not be used hereinafter" is displayed. Further, in the example illustrated in the right part of FIG. 26, by performing display control so that the pacemaker 30 gives a predetermined hand sign 49, it is possible to convey an unavailable operation input mode to the user. The user can recognize an unavailable operation input mode by remembering the predetermined hand sign.

In this manner, by notifying the user of unavailable operation input modes, the user can clearly recognize limitation of the operation input mode, so that it is possible to improve user-friendliness. Note that notification to the user is not limited to unavailable operation input modes, and the user may be notified of available operation input methods.

<4-2. Communication UI>

FIG. 27 and FIG. 28 illustrate examples of a communication UI according to an embodiment. For example, when the user relaxes, or is on a break at a cafe, or the like (behavior can be recognized through image recognition, or the like), as illustrated in an upper part of FIG. 27, the information processing apparatus 1 performs control such that avatars 50 and 51 are displayed in front of the eyes (for example, on a table (real object)). These avatars 50 and 51 correspond to communication application, and, for example, are generated by synthesizing a face image of a counterpart user from which newly arriving message (message through sound, text or an image) is received. Further, behavior in a state where the user relaxes can be recognized based on, for example, biological information. The biological information can include, for example, a heart rate, a body temperature, diaphoresis, a blood pressure, a pulse, aspiration, eyeblink, eyeball motion, a gazing period, a pupil diameter, a brain wave, body motion, a body position, a skin temperature, skin electric resistance, myopotential, or the like.

The user can naturally select an avatar by seeing an avatar in which the user is interested (input using the line of sight) or turning his/her head (face) to the avatar in which the user is interested (head gesture). The selected avatar approaches the user.

Subsequently, as illustrated in a middle part of FIG. 27, when there is only the selected avatar 50, as illustrated in a lower part of FIG. 27, a newly arriving message 52 from the counterpart user corresponding to the avatar 50 is displayed, so that the user can confirm the message from the counterpart user.

Subsequently, as illustrated in an upper part of FIG. 28, icons 53 and 54 which are options for reply are displayed on a table (real object). The icon 53 is used for replying a current location of the user using map data. Further, the icon 54 for reply is used for replying through sound input. The user can naturally select an icon which the user desires to execute by seeing the icon (option) (input using the line of sight) or by turning his/her head (face) to a direction of the option which the user desires to execute.

For example, when the user selects the icon 54 by turning his/her eyes to the icon 54, as illustrated in the middle part of FIG. 28, the color or shape of the icon 54 changes, so that the user can recognize that he/she selects the icon 54. When user utterance (sound input) is detected by the microphone 112, as illustrated in the lower part of FIG. 28, the information processing apparatus 1 displays animation that the icon 43 flies to the avatar 50, so that the user is notified that transmission of the message is completed.

Further, selection of the avatar is not limited to the above-described motion of the line of sight or head, and the avatar may be selected through behavior that the user actually approaches the avatar. The behavior of approaching the avatar can be recognized through space recognition using a shot image.

In this manner, it is possible to naturally encourage user selection operation by coordinating the user selection behavior (motion of the line of sight or the head, behavior recognition) with motion of the UI.

Note that the displayed avatar is not limited to the above-described counterpart user of the newly arriving message as described above, and may be, for example, a counterpart user with whom the user daily exchanges messages, a counterpart user with whom the user has exchanged a message recently, a counterpart user with whom the user makes an appointment of meeting or call at recent time based on the user's schedule, or the like.

5. CONCLUSION

As described above, the information processing apparatus 1 according to an embodiment of the present disclosure, it is possible to further improve operability by dynamically switching the operation input mode according to the state of user activity.

By this, it is possible to reduce erroneous operation, so that the user can use the apparatus at ease.

Further, by dynamically switching the operation input mode while taking into account recognition accuracy, it is possible to realize input through an UI which is tolerant of change even outdoors where the environment is likely to change, or while the user plays sports.

Further, because the information processing apparatus 1 is realized with smart glasses and operation input without using hands such as input using the line of sight, head gesture and input which uses space recognition are variously provided, it is possible to improve operability.

It should be understood by those skilled in the art that various modifications, combinations, sub-combinations and alterations may occur depending on design requirements and other factors insofar as they are within the scope of the appended claims or the equivalents thereof.

For example, it is also possible to create a computer program for causing hardware such as a CPU, a ROM and a RAM incorporated in the above-described information processing apparatus 1 to exert functions of the information processing apparatus 1. Further, a computer readable storage medium which has the computer program stored therein is also provided.

Further, the operation input modes according to the states illustrated in FIG. 3 to FIG. 7 can be arbitrarily combined, and combination is not limited to the examples illustrated in FIG. 3 to FIG. 7. The combination of the operation input mode according to the states may be different for each user. For example, in the case of a user who is less likely to perform erroneous operation even when the amount of activity is high, it is also possible to increase available operation input modes when the amount of activity is high.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

(1)
An information processing apparatus including:
circuitry configured to
acquire information associated with a user situation,
determine a display mode based on the information associated with the user situation, and allow an operation unit to receive a user input based on a target displaying in the determined display mode.

(2)
The information processing apparatus according to (1), wherein the circuitry is further configured to enable an operation input mode associated with the user input.

(3)
The information processing apparatus according to (1) or (2), wherein the user situation includes a speed of a user.

(4)
The information processing apparatus according to any of (1) to (3), wherein the user situation includes traffic condition, road condition, time or weather information.

(5)
The information processing apparatus according to any of (1) to (4), wherein the user situation includes an amount of a user activity.

(6)
The information processing apparatus according to any of (1) to (5), wherein the circuitry is further configured to turn off the display mode when the amount of the user activity is greater than a predetermined threshold.

(7)
The information processing apparatus according to any of (1) to (6), wherein the user situation includes an amount of a user activity, and
wherein the circuitry is further configured to disable the operation input mode when the amount of the user activity is large.

(8)
The information processing apparatus according to any of (1) to (7), wherein the user situation includes an amount of a user activity, and
wherein the circuitry is further configured to reduce a number of input capabilities associated with the operation input mode when the amount of the user activity increases.

(9)
The information processing apparatus according to any of (1) to (8), wherein each of the input capabilities is represented as a virtual object.

(10)
The information processing apparatus according to any of (1) to (9), wherein the user situation includes an amount of a user activity, and
wherein the circuitry is further configured to increase a number of input capabilities associated with the operation input mode when the amount of the user activity decreases.

(11)
The information processing apparatus according to any of (1) to (10), wherein the circuitry is further configured to disable a first input capability associated with the operation input mode when the amount of the user activity increases.

(12)
The information processing apparatus according to any of (1) to (11), wherein the first input capability is associated with a space recognition.

(13)
The information processing apparatus according to any of (1) to (12), wherein the circuitry is further configured to allow a second input capability, which is associated with the operation input mode when the first input capability is disabled.

(14)
The information processing apparatus according to any of (1) to (13), wherein the circuitry is further configured to change a combination of input capabilities associated with the operation input mode when the amount of the user activity is changed.

(15)
The information processing apparatus according to any of (1) to (14), wherein the user situation is associated with a user riding a bike.

(16)
The information processing apparatus according to any of (1) to (15), wherein the user situation is associated with a user riding in a car.

(17)
The information processing apparatus according to any of (1) to (16), wherein the circuitry is further configured to detect the user situation using at least one of:
space recognition;
line of sight recognition;
head posture recognition; or
sound recognition.

(18)
The information processing apparatus according to any of (1) to (17), wherein the information processing apparatus is a wearable apparatus, and
the information processing apparatus further includes a display unit.

(19)
An information processing apparatus method, the method being executed via at least one processor having circuitry, and including:
acquiring information associated with a user situation;
determining a display mode based on the information associated with the user situation, and allowing an operation unit to receive a user input based on a target displaying in the determined display mode.

(20)
A non-transitory computer-readable storage medium having embodied thereon a program, which when executed by a computer causes the computer to execute a method, the method including:
acquiring information associated with a user situation;
determining a display mode based on the information associated with the user situation, and
allowing an operation unit to receive a user input based on a target displaying in the determined display mode.

(21)
An information processing apparatus including:
a selecting unit that selects one or more operation input methods according to information regarding user activity,
wherein the selecting unit selects a first operation input method for causing an operation target to operate in first operation when a state of the user activity is determined to be a first state, and
the selecting unit selects a second operation input method for causing the operation target to operate in second operation different from the first operation when the state of the user activity is determined to be a second state.

(22)
The information processing apparatus according to (21), further including:
a determining unit that determines a display mode of the operation target according to the selected operation input method,
wherein the operation target is displayed in a first display mode determined by the determining unit when the first operation input method is selected, and
the operation target is displayed in a second display mode different from the first display mode determined by the determining unit when the second operation input method is selected.

(23)
The information processing apparatus according to (22), further including:
an accepting unit that accepts user operation input with respect to the operation target,
wherein information to be used by the accepting unit to accept the user operation input is different according to the operation input method selected by the selecting unit.

(24)
The information processing apparatus according to (23), wherein the operation target is a target for selection, and the accepting unit accepts operation of selecting the operation target as the operation input of the user.

(25)
The information processing apparatus according to (24), further including:
a generating unit that generates a display image of the target for selection according to the determined display mode.

(26)
The information processing apparatus according to any one of (21) to (25),
wherein the activity state is recognized based on an amount of activity included in the information regarding the user activity.

(27)
The information processing apparatus according to (23), wherein the accepting unit accepts the user operation input based on information detected by a sensor.

(28)
The information processing apparatus according to (27), wherein the selecting unit selects the operation input method according to an accuracy score of a recognition engine which performs recognition based on the information detected by the sensor.

(28)
The information processing apparatus according to (27), wherein the selecting unit selects the first operation input method for causing the operation target to operate in the first operation when the accuracy score falls below a threshold, and
the selecting unit selects the second operation input method for causing the operation target to operate in the second operation different from the first operation when the accuracy score exceeds the threshold.

(30)
The information processing apparatus according to (29), wherein the recognition engine is at least any of a head posture recognition engine, a depth recognition engine, a SLAM recognition engine, a line of sight recognition engine, an orientation recognition engine and a sound recognition engine.

(31)
The information processing apparatus according to (25), further including:
a display control unit that performs control so that the display image of the target for selection is displayed at a display unit, the display image being generated by the generating unit,
wherein feedback control of user operation of selecting the target for selection is different according to the selected operation input method, the feedback control being performed by the display control unit.

(32)
The information processing apparatus according to (31), wherein the information processing apparatus is a wearable apparatus which is worn on a head, and
the information processing apparatus further includes a display unit that is located in front of eyes of the user when the user wears the information processing apparatus.

(33)
The information processing apparatus according to (32), wherein the display unit is a transmissive display unit, and the display control unit performs control so that the generated display image of the target for selection is displayed while being superimposed on a real object in real space.

(34)
The information processing apparatus according to any one of (21) to (33),
wherein the operation input method is at least any of input which uses space recognition, input which uses head gesture, input using a line of sight and sound input.

(35)
The information processing apparatus according to (25), wherein the number of targets for selection generated by the generating unit is different according to the selected operation input method.

(36)
An information processing method including:
selecting by a processor one or more operation input methods according to information regarding user activity,
wherein in the selection,
a first operation input method for causing an operation target to operate in first operation is selected when a state of the user activity is determined to be a first state, and
a second operation input method for causing the operation target to operate in second operation different from the first operation is selected when the state of the user activity is determined to be a second state.

(37)

A program causing a computer to function as:
a selecting unit that selects one or more operation input methods according to information regarding user activity, wherein the selecting unit selects a first operation input method for causing an operation target to operate in first operation when a state of the user activity is determined to be a first state, and
the selecting unit selects a second operation input method for causing the operation target to operate in second operation different from the first operation when the state of the user activity is determined to be a second state.

REFERENCE SIGNS LIST 1 information processing apparatus
10 control unit
100 recognition engine
100a head posture recognition engine
100b depth recognition engine
100c SLAM recognition engine
100d line of sight recognition engine
100e sound recognition engine
100f position recognition engine
101 score acquiring unit
102 behavior recognizing unit
103 input method selecting unit
104 display mode determining unit
105 display information generating unit
106 display control unit
107 operation input accepting unit
110 camera
111 camera
112 microphone
113 gyro sensor
114 acceleration sensor
115 orientation sensor
116 position measuring unit
121 score acquiring unit
123 input method selecting unit
11 sensor unit
12 operation input unit
13 display unit
14 speaker
15 communication unit
16 storage unit

The invention claimed is:

1. An information processing apparatus, comprising:
circuitry configured to:
acquire, from a motion sensor of a mobile terminal, activity information associated with an activity amount of the mobile terminal;
acquire a captured image of a real space from an outward camera of the mobile terminal;
acquire sensor information from a specific sensor different from the outward camera and the motion sensor,
wherein the specific sensor is configured to acquire information associated with at least one of a line-of-sight input, a gesture input, or a sound input;
execute, based on an image recognition of the captured image, a space recognition to recognize a three-dimensional position of a user of the mobile terminal;
set, based on the three-dimensional position, an operation-input mode of the mobile terminal to a first operation-input mode;
control, in the first operation-input mode, a display of the mobile terminal to arrange a virtual object three-dimensionally in the real space, wherein the arrangement of the virtual object is based on the three-dimensional position;
receive, in the first operation-input mode, a first operation input based on the three-dimensional position to select the virtual object;
determine, based on the activity information, whether a state of the mobile terminal is changed from a first state to a second state, wherein the activity amount in the second state is larger than the activity amount in the first state;
switch, based on the determination that the state of the mobile terminal is changed from the first state to the second state, the operation-input mode from the first operation-input mode of the mobile terminal to a second operation-input mode; and
receive, in the second operation-input mode, a second operation input based on the sensor information, while disabling the first operation input, wherein the sensor information is different from the captured image.

2. The information processing apparatus according to claim 1, wherein
the specific sensor is an inward camera of the mobile terminal, and
the circuitry is further configured to recognize, as the second operation input, the line-of-sight input based on the sensor information.

3. The information processing apparatus according to claim 2, wherein the display is a wearable display.

4. The information processing apparatus according to claim 1, wherein the circuitry is further configured to:
determine, based on the activity information, whether the state of the mobile terminal is changed from the second state to a third state, wherein the activity amount in the third state is larger than the activity amount in the second state; and
disable the first operation input and the second operation input.

5. The information processing apparatus according to claim 1, wherein
the virtual object includes a plurality of virtual objects, and
the number of the plurality of virtual objects in the first operation-input mode is larger than the number of the plurality of virtual objects in the second operation-input mode.

6. A method for providing a multi-modal user interface, the method comprising:
in an information processing apparatus comprising circuitry:
acquiring, from a motion sensor of a mobile terminal, activity information associated with an activity amount of the mobile terminal;
acquiring a captured image of a real space from an outward camera of the mobile terminal;
acquiring sensor information from a specific sensor different from the outward camera and the motion sensor,
wherein the specific sensor is configured to acquire information associated with at least one of a line-of-sight input, a gesture input, or a sound input;

executing, based on an image recognition of the captured image, a space recognition to recognize a three-dimensional position of a user of the mobile terminal;

setting, based on the three-dimensional position, an operation-input mode of the mobile terminal to a first operation-input mode;

controlling, in the first operation-input mode, a display of the mobile terminal to arrange a virtual object three-dimensionally in the real space, wherein the arrangement of the virtual object is based on the three-dimensional position;

receiving, in the first operation-input mode, a first operation input based on the three-dimensional position to select the virtual object;

determining, based on the activity information, whether a state of the mobile terminal is changed from a first state to a second state, wherein the activity amount in the second state is larger than the activity amount in the first state;

switching, based on the determination that the state of the mobile terminal is changed from the first state to the second state, the operation-input mode from the first operation-input mode to a second operation-input mode; and receiving, in the second operation-input mode, a second operation input based on the sensor information, while disabling the first operation input, wherein the sensor information is different from the captured image.

7. A non-transitory computer-readable storage medium having stored thereon computer-executable instructions which, when executed by a computer, cause the computer to execute operations, the operations comprising:

acquiring, from a motion sensor of a mobile terminal, activity information associated with an activity amount of the mobile terminal;

acquiring a captured image of a real space from an outward camera of the mobile terminal;

acquiring sensor information from a specific sensor different from the outward camera and the motion sensor, wherein the specific sensor is configured to acquire information associated with at least one of a line-of-sight input, a gesture input, or a sound input;

executing, based on an image recognition of the captured image, a space recognition to recognize a three-dimensional position of a user of the mobile terminal;

setting, based on the three-dimensional position, an operation-input mode of the mobile terminal to a first operation-input mode;

controlling, in the first operation-input mode, a display of the mobile terminal to arrange a virtual object three-dimensionally in the real space, wherein the arrangement of the virtual object is based on the three-dimensional position;

receiving, in the first operation-input mode, a first operation input based on the three-dimensional position to select the virtual object;

determining, based on the activity information, whether a state of the mobile terminal is changed from a first state to a second state, wherein the activity amount in the second state is larger than the activity amount in the first state;

switching, based on the determination that the state of the mobile terminal is changed from the first state to the second state, the operation-input mode from the first operation-input mode to a second operation-input mode; and receiving, in the second operation-input mode, a second operation input based on the sensor information, while disabling the first operation input, wherein the sensor information is different from the captured image.

* * * * *